US010908433B2

(12) United States Patent
Mitsui

(10) Patent No.: US 10,908,433 B2
(45) Date of Patent: Feb. 2, 2021

(54) ORTHOKERATOLOGY LENS DESIGNATING METHOD, DESIGNATING SYSTEM, DESIGNATING AND SUPPLYING METHOD, AND DESIGNATING AND SUPPLYING SYSTEM

(71) Applicant: MITSUI MEDICAL COMMERCE CO., LTD., Tokyo (JP)

(72) Inventor: Iwane Mitsui, Tokyo (JP)

(73) Assignee: MITSUI MEDICAL COMMERCE CO, LTD., Tokyo (JP)

( * ) Notice: Subject to any disclaimer, the term of this patent is extended or adjusted under 35 U.S.C. 154(b) by 258 days.

(21) Appl. No.: 16/314,302

(22) PCT Filed: Jun. 30, 2017

(86) PCT No.: PCT/JP2017/024118
§ 371 (c)(1),
(2) Date: Dec. 28, 2018

(87) PCT Pub. No.: WO2018/003967
PCT Pub. Date: Jan. 4, 2018

(65) Prior Publication Data
US 2020/0387010 A1    Dec. 10, 2020

(30) Foreign Application Priority Data

Jun. 30, 2016  (JP) .................................. 2016-130262
Jun. 29, 2017  (JP) .................................. 2017-127653

(51) Int. Cl.
G02C 7/00      (2006.01)
G02C 7/02      (2006.01)
(Continued)

(52) U.S. Cl.
CPC ............. *G02C 7/047* (2013.01); *G02C 7/048* (2013.01); *A61F 9/013* (2013.01); *G02C 2202/24* (2013.01)

(58) Field of Classification Search
CPC ... G02C 7/00; G02C 7/02; G02C 7/04; G02C 7/06; G02C 7/021; G02C 7/027;
(Continued)

(56) References Cited

U.S. PATENT DOCUMENTS 5,695,509 A     12/1997  El Hage
6,361,169 B1 *  3/2002   Tung ...................... A61B 3/107
                                                    351/219
(Continued)

FOREIGN PATENT DOCUMENTS

CN    102549479 A    7/2012
CN    103505197 A    1/2014
(Continued)

OTHER PUBLICATIONS

Jan. 10, 2019 International Preliminary Report on Patentability issued in International Patent Application No. PCT/JP2017/024118.
(Continued)

*Primary Examiner* — Mustak Choudhury
(74) *Attorney, Agent, or Firm* — Oliff PLC

(57) ABSTRACT

An orthokeratology lens designating system 10 includes a selecting device 20, a database server 30, a lens designating server 50 and a terminal device 70. The selecting device 20 includes a device 22 for acquiring movement data of an orthokeratology lens moving on a cornea with the orthokeratology lens mounted on the cornea, and an assessing device 28 for assessing, on the basis of the lens movement data, that the orthokeratology lens is a registered lens that can be used for a patient. Registered lens correction D data of the registered lens, registered patient data including
(Continued)

registered cornea D data of a cornea, and registration stage data that indicates in which stage of a plurality of correction stages, the lens is to be mounted on the cornea, are output to the database server 30. The database server 30 is configured to accept and store these pieces of data to build a database. The terminal device 70 includes a patient data acquiring device 71 and a patient stage data accepting means, and is capable of transmitting patient data and patient stage data to the lens designating server 50. The lens designating server 50 is configured to retrieve from the database a registered lens having registered data that are the same as or close to the received patient data and patient stage data, and to designate the retrieved registered lens as the orthokeratology lens to be used for the patient.

27 Claims, 11 Drawing Sheets

(51) Int. Cl.
*G02C 7/04* (2006.01)
*A61F 9/013* (2006.01)

(58) Field of Classification Search
CPC ........ G02C 7/041; G02C 7/044; G02C 7/045; G02C 7/047; G02C 7/048; G02C 7/049; G02C 2202/24; A61F 9/0017; A61F 9/007; A61F 9/013; A61F 2/14; A61F 2/142; A61B 3/11; A61B 3/103; A61B 3/107; A61B 3/112; A61B 3/145; G02B 1/043
See application file for complete search history.

(56) References Cited

U.S. PATENT DOCUMENTS

| | | | |
|---|---|---|---|
| 6,582,077 | B1 | 6/2003 | Tabb et al. |
| 7,762,667 | B2 | 7/2010 | Andino et al. |
| 2009/0303442 | A1* | 12/2009 | Choo ............... G02C 7/047 351/246 |
| 2010/0302509 | A1 | 12/2010 | Steinmuller |
| 2011/0025979 | A1 | 2/2011 | Chehab et al. |
| 2014/0002799 | A1 | 1/2014 | Wildsmith |
| 2014/0362341 | A1* | 12/2014 | Yoon ............... G02C 7/047 351/159.74 |
| 2016/0124245 | A1 | 5/2016 | Wildsmith et al. |
| 2016/0170232 | A1 | 6/2016 | Wildsmith |

FOREIGN PATENT DOCUMENTS

| | | | |
|---|---|---|---|
| JP | 2006-043150 A | 2/2006 | |
| JP | 2006043150 A * | 2/2006 | ............. G02C 7/047 |
| JP | 3881221 B2 | 2/2007 | |
| JP | 2009-544436 A | 12/2009 | |
| JP | 2011-189192 A | 9/2011 | |
| JP | 2002-350786 A | 12/2012 | |
| JP | 2015-503769 A | 2/2015 | |
| WO | 2011/014510 A1 | 2/2011 | |
| WO | 2013/110059 A1 | 7/2013 | |

OTHER PUBLICATIONS

Jan. 1, 2019 International Preliminary Report on Patentability issued in International Patent Application No. PCT/JP2017/024118.
Feb. 20, 2020 Extended European Search Report issued in European Patent Application No. 17820321.2.
Sep. 12, 2017 International Search Report issued in International Patent Application No. PCT/JP2017/024118.

* cited by examiner

ORTHOKERATOLOGY LENS DESIGNATING METHOD, DESIGNATING SYSTEM, DESIGNATING AND SUPPLYING METHOD, AND DESIGNATING AND SUPPLYING SYSTEM

TECHNICAL FIELD

The present invention relates to a designating method, a designating system and a designating and supplying method, and a designating and supplying system for an orthokeratology lens, which is a contact lens used for a cornea correction treatment in which mounting the contact lens having a special curve design changes and corrects the shape of a cornea in order to treat an ophthalmological refractive abnormality such as myopia, hyperopia, or presbyopia.

BACKGROUND ART

Out of cornea correction treatments, a conventional treatment described in, for example, Patent Literature 1 for correcting myopia and astigmatism is referred to as orthokeratology.

Patent Literature 2 discloses an orthokeratology lens that is a contact lens for correcting myopia and/or astigmatism (hereinafter, referred to as an orthokeratology lens including the contact lens for correcting the myopia and/or astigmatism and a contact lens for correcting hyperopia and/or presbyopia) according to the invention by the present inventor.

The curvature of the orthokeratology lens is flattened stepwise (in stages) in the case of correcting myopia, while the curvature of the orthokeratology lens is tightened stepwise in the case of correcting hyperopia or presbyopia. In the final stage, a cornea comes to have a curvature so as to have an ideal uncorrected vision.

Conventionally, to mount an orthokeratology lens on a cornea, a plurality of candidate contact lenses, which are selected on the basis of data of a patient's corneal refractive power (hereinafter referred to as diopter or D) measured by a keratometer, are sequentially mounted. One of the contact lenses that has an optimal correction D to correct the cornea D is used as the orthokeratology lens.

In some instances, a lot of contact lenses having slightly different correction D are prepared, and all of them are tested on a patient's cornea. In the instances, since one of the contact lenses is used for correction, while the others are discarded, there are problems that many lenses are wasted, and an increased burden is imposed on the patient.

Since the number of doctors who specialize in vision correction treatment using orthokeratology lenses as described above is low and the areas where such doctors are present are limited, the treatment imposes quite temporal and economic burdens on patients who live in distant locations. In the distant locations, even if the doctors are present, the doctors have technical and temporal difficulties in getting optimal orthokeratology lenses for the patients.

CITATION LIST

Patent Literature

Patent Literature 1: U.S. Pat. No. 5,695,509
Patent Literature 2: Japanese Patent No. 3881221

SUMMARY OF INVENTION

Technical Problem

The present invention has been made in view of the conventional problems described above, and an object of the present invention is to provide an orthokeratology lens designating method and an orthokeratology lens designating system that quickly designate an optimal contact lens for orthokeratology, i.e. orthokeratology lens, without the need to mount contact lenses on a patient's cornea again and again and impose a burden on the patient, and to provide an orthokeratology lens designating and supplying method and an orthokeratology lens designating and supplying system that designate and supply the orthokeratology lens.

Solution to Problem

The present inventor has developed a method for easily finding out an orthokeratology lens that is optimally mounted on a patient's cornea. The present inventor has built a database that accumulates data about orthokeratology lenses actually used for correcting corneas of ten thousand or more patients, by using this method. The present inventor has made it possible to easily designate an optimal orthokeratology lens, on the basis of the database, from a patient's corneal data acquired by a doctor. Furthermore, data about the designated orthokeratology lens is transmitted to a terminal of the doctor, and is transmitted therefrom to a lens manufacturing device. The orthokeratology lens is then manufactured with the lens manufacturing device, and is supplied to the doctor.

Namely, the above object is solved by the following embodiments.

(1) An orthokeratology lens designating method includes a database building process of repeating a trial process in which a mounting process of mounting an orthokeratology lens on a cornea at a position centering on a pupil of a patient whose head is in an erect state, an image information acquiring process of continuously or intermittently acquiring images of the orthokeratology lens moving on the cornea, and a movement data detecting process of detecting a movement speed and a movement direction of the orthokeratology lens from the acquired image information are sequentially performed on a plurality of orthokeratology lenses, and a selection process of determining whether or not data of the acquired movement speed and movement direction is within a certain range, and when the data is within the certain range, selecting a lens as the orthokeratology lens to be used for the patient in order to build a lens database, provided that the selected orthokeratology lens is assigned as a registered lens, by storing registered patient data that includes at least registered cornea D data, out of registered lens correction D data having lens correction D data of the registered lens at a contact portion with the cornea, the registered cornea D data having D data of the cornea at the contact portion before mounting the registered lens, registered corneal diameter data having corneal diameter data of the patient, and registered pupil diameter data having pupil diameter data of the patient, and registration stage data having data that indicates in which stage of a plurality of correction stages, including first, second, and later stages, the registered lens is mounted on the cornea;

a patient data acquiring process of acquiring patient data including at least patient cornea D data, out of the patient cornea D data having D data of a patient's cornea to be corrected, patient corneal diameter data having data of a corneal diameter, and patient pupil diameter data having data of a pupil diameter;

a patient stage data acquiring process of acquiring patient stage data that indicates which stage of a plurality of correction stages the present mounting of an orthokeratology lens corresponds to, on the patient's cornea to be corrected; and a lens designating process of retrieving the registered lens having the registered cornea D data that is the closest to the acquired patient cornea D data and the same registration stage data as the patient stage data in the lens database, and designating the retrieved registered lens as an orthokeratology lens to be used for the patient.

(2) An orthokeratology lens designating system includes a selecting device, a database server, a lens designating server connected to the database server, and a terminal device that can be connected to the lens designating server, the selecting device includes a lens movement data acquiring device that includes a lens imaging camera configured to image an orthokeratology lens mounted on a cornea at a position centering on a pupil of a patient whose head is in an erect state to continuously or intermittently acquire images of the orthokeratology lens moving on the cornea, and a lens movement data detecting device configured to detect lens movement data having data about at least a movement speed and a movement direction of the orthokeratology lens from the image information of the orthokeratology lens moving on the cornea acquired by the lens imaging camera; and an assessing device configured to determine whether or not the acquired lens movement data is within a certain range, and assess the orthokeratology lens that is within the certain range as an orthokeratology lens suited for use for the patient, the selecting device is configured such that, provided that the orthokeratology lens that is suited for use for the patient is assigned as a registered lens, registered lens correction D data having data of lens correction D of the registered lens at a contact portion with the cornea of the patient, registered patient data including at least registered cornea D data, out of the registered cornea D data having D data of the cornea to be corrected at the contact portion, registered corneal diameter data having corneal diameter data of the patient, and registered pupil diameter data, and registration stage data having data that indicates in which stage of a plurality of correction stages, including first, second, and later stages, the registered lens is mounted on the cornea are outputted to the database server, the database server is configured to build a database by storing the registered patient data and the registration stage data on the registered lens, the terminal device includes a patient data acquiring device configured to acquire patient data including at least patient cornea D data, out of the patient cornea D data having D data of a patient's cornea to be corrected, patient corneal diameter data having data of a corneal diameter, and patient pupil diameter data having data of a pupil diameter; and a patient stage data acquiring device configured to acquire patient stage data that indicates in which stage of a plurality of correction stages, including first, second, and later stages, the next orthokeratology lens is mounted on the patient's cornea to be corrected, and the terminal device is configured to be capable of transmitting the patient data and the patient stage data to the lens designating server, and the lens designating server is configured to retrieve the registered lens having the registered cornea D data that is the closest to the acquired patient cornea D data and the same registration stage data as the patient stage data in the database, and designate the retrieved registered lens as an orthokeratology lens to be used for the patient.

(3) An orthokeratology lens designating and supplying method includes:

a database building process of repeating a trial process in which a mounting process of mounting an orthokeratology lens on a cornea at a position centering on a pupil of a patient whose head is in an erect state, an image information acquiring process of continuously or intermittently acquiring images of the orthokeratology lens moving on the cornea, and a movement data detecting process of detecting a movement speed and a movement direction of the orthokeratology lens from the acquired image information are sequentially performed on a plurality of orthokeratology lenses, and a selection process of determining whether or not data of the acquired movement speed and movement direction is within a certain range, and when the data is within the certain range, selecting a lens as the orthokeratology lens to be used for the patient; in order to build a lens database, provided that the selected orthokeratology lens is assigned as a registered lens, by storing registered patient data that includes at least registered cornea D data, out of registered lens correction D data having lens correction D data of the registered lens at a contact portion with the cornea, the registered cornea D data having D data of the cornea at the contact portion before mounting the registered lens, registered corneal diameter data having corneal diameter data of the patient, and registered pupil diameter data having pupil diameter data of the patient, and registration stage data having data that indicates in which stage of a plurality of correction stages, including first, second, and later stages, the registered lens is mounted on the cornea, a patient data acquiring process of acquiring patient data including at least patient cornea D data, out of the patient cornea D data having D data of a patient's cornea to be corrected, patient corneal diameter data having data of a corneal diameter, and patient pupil diameter data having data of a pupil diameter, a patient stage data acquiring process of acquiring patient stage data that indicates which stage of a plurality of correction stages the present mounting of an orthokeratology lens corresponds to, on the patient's cornea to be corrected, a lens designating process of retrieving the registered lens having the registered cornea D data that is the closest to the acquired patient cornea D data and the same registration stage data as the patient stage data in the lens database, and designating the retrieved registered lens as an orthokeratology lens to be used for the patient, a registered lens correction D data transmitting process of transmitting the registered lens correction D data of the designated orthokeratology lens to a lens manufacturing device, and a lens manufacturing process of accepting the transmitted registered lens correction D data, and manufacturing the orthokeratology lens to be used for the patient on the basis of the registered lens correction D data.

(4) An orthokeratology lens designating and supplying system includes a selecting device, a database server, a lens designating server connected to the database server, a terminal device that can be connected to the lens designating server, and a lens manufacturing device, the selecting device includes a lens movement data acquiring device that includes a lens imaging camera configured to image an orthokeratology lens mounted on a cornea at a position centering on a pupil of a patient whose head is in an erect state to continuously or intermittently acquire images of the orthokeratology lens moving on the cornea, and a lens movement data detecting device configured to detect lens movement data having data about at least a movement speed and a movement direction of the orthokeratology lens from image information of the orthokeratology lens moving on the cornea acquired by the lens imaging camera; and an assessing device configured to determine whether or not the acquired lens movement data is within a certain range, and assess the orthokeratology lens that is within the certain range as an orthokeratology lens suited for use for the patient, the selecting device is configured such that, provided that the orthokeratology lens that is suited for use for the patient is assigned as a registered lens, registered lens correction D data having data of lens correction D of the registered lens at a contact portion with the cornea of the patient, registered patient data including at least registered cornea D data, out of the registered cornea D data having D data of the cornea to be corrected at the contact portion, registered corneal diameter data having corneal diameter data of the patient, and registered pupil diameter data, and registration stage data having data that indicates in which stage of a plurality of correction stages, including first, second, and later stages, the registered lens is mounted on the cornea are outputted to the database server, the database server is configured to build a database by storing the registered patient data and the registration stage data on the registered lens, the terminal device includes a patient data acquiring device configured to acquire patient data including at least patient cornea D data, out of the patient cornea D data having D data of a patient's cornea to be corrected, patient corneal diameter data having data of a corneal diameter, and patient pupil diameter data having data of a pupil diameter; and a patient stage data acquiring device configured to acquire patient stage data that indicates in which stage of the plurality of correction stages, including the first, second, and later stages, the next orthokeratology lens is mounted on the patient's cornea to be corrected, and the terminal device is configured to be capable of transmitting the patient data and the patient stage data to the lens designating server, the lens designating server is configured to retrieve the registered lens having the registered cornea D data that is the closest to the acquired patient cornea D data and the same registration stage data as the patient stage data in the database, and to designate the retrieved registered lens as an orthokeratology lens to be used for the patient, and the lens manufacturing device is configured to manufacture the same lens as the registered lens, as an orthokeratology lens to be mounted on the patient, on the basis of the registered lens correction D data of the designated orthokeratology lens.

Advantageous Effects of Invention

According to the present invention, on the basis of the patient data having the patient cornea D data of the patient's cornea and the patient stage data that indicates which stage of a plurality of correction stages for the same patient the orthokeratology lens is in, the registered lens data having similar data is retrieved in the lens database and the optimal orthokeratology lens can be designated and manufactured, thereby quickly supplying a doctor who is located at a distance with the optimal orthokeratology lens. Thus, the present invention can have the effect of significantly reducing a load of a patient and the occurrence of waste lenses.

DESCRIPTION OF EMBODIMENTS

An embodiment of the present invention will be described below in detail with reference to the drawings.

Embodiment

Figure 1:
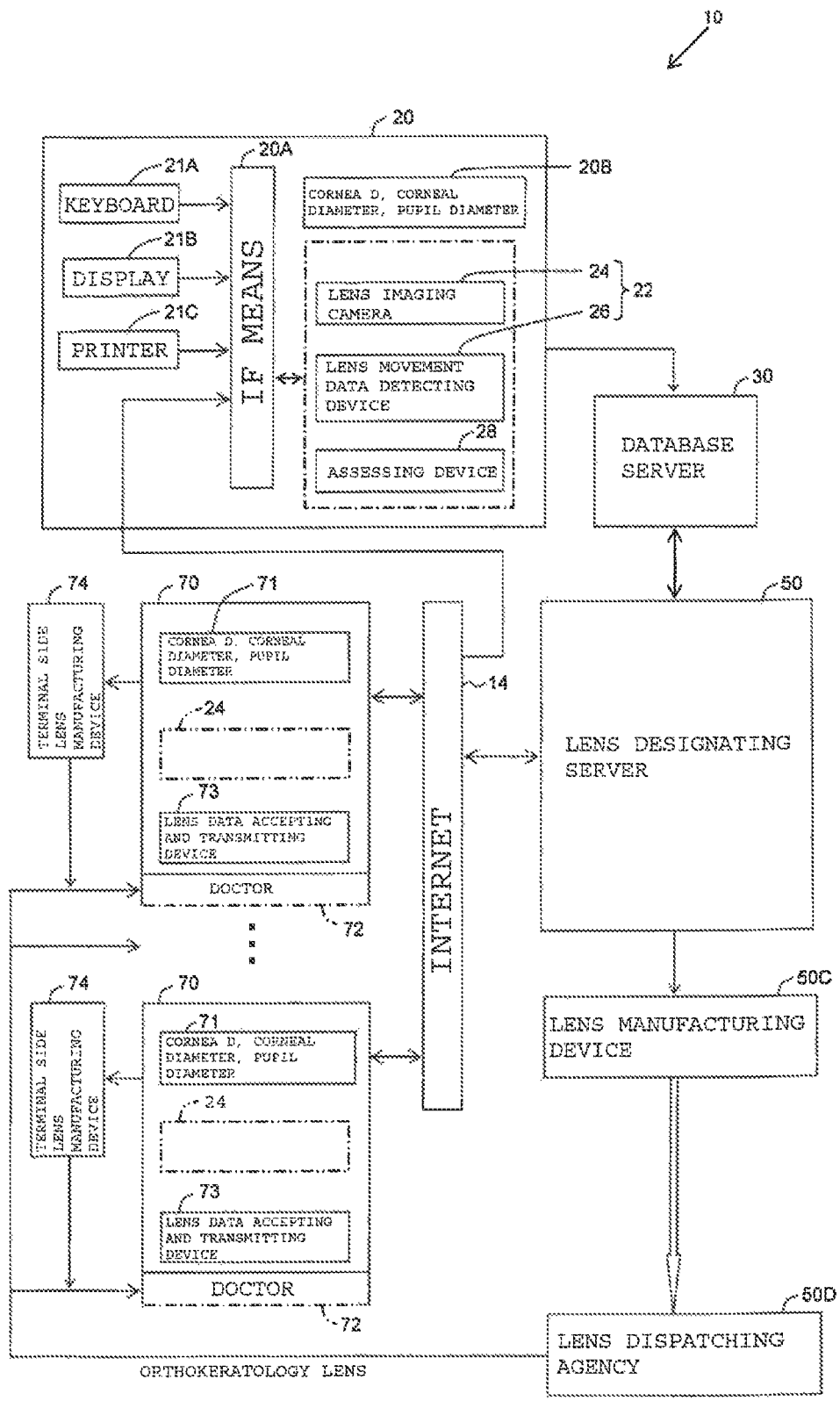
FIG. 1 is a block diagram showing a configuration of an orthokeratology lens designating and supplying system according to an embodiment of the present invention.

As illustrated in FIG. 1, an orthokeratology lens designating and supplying system (hereinafter referred to as designating and supplying system) 10 for orthokeratology according to an embodiment of the present invention is configured to include a selecting device 20, a database server 30, a lens designating server 50 as a main server, a lens manufacturing device 50C connected to the lens designating server 50, terminal devices 70 that can be connected to the lens designating server 50, and terminal side lens manufacturing devices 74.

The correspondence relationship between the above-described respective configurations will be schematically described.

In the selecting device 20 in the designating and supplying system 10 according to the embodiment, a lens movement data acquiring device 22 acquires data about a movement direction and a movement speed of an orthokeratology lens immediately after the orthokeratology lens is mounted on a patient's cornea. An assessing device 28 assesses whether or not the movement direction and the movement speed are optimal for the patient's cornea.

The database server 30 is configured to build a database 30B (refer to FIG. 2) by repeating a process of storing data on an orthokeratology lens (registered lens) that is assessed to be usable (positive) and data on the patient's cornea.

As illustrated in FIG. 1, the terminal devices 70 and the terminal side lens manufacturing devices 74 are located at distances from the lens designating server 50, for example, beside doctors 72 who are abroad, at domestic distant locations, or the like. The terminal device 70 is configured to be capable of transmitting patient data, including patient cornea D data on a patient's cornea acquired by measurement by the doctor 72, to the lens designating server 50.

The lens designating server 50 is configured to retrieve a registered lens having similar data to the received patient data in the database 30B of the database server 30, and designate the lens as an optimal orthokeratology lens.

Upon designating the orthokeratology lens by the lens designating server 50, as illustrated in FIG. 1, lens data of the designated orthokeratology lens is transmitted to a lens data accepting and transmitting device 73 of the terminal device 70. The lens data accepting and transmitting device 73 outputs a manufacturing command signal, together with the lens data of the designated orthokeratology lens, to the terminal side lens manufacturing device 74. The terminal side lens manufacturing device 74 thereby manufactures an orthokeratology lens having the lens data. The doctor 72 acquires the manufactured orthokeratology lens, and uses the orthokeratology lens for the patient.

When no orthokeratology lens is manufactured by the terminal side lens manufacturing device 74, the lens manufacturing device 50C manufactures an orthokeratology lens. The manufactured orthokeratology lens is sent by a lens dispatching agency 50D to the doctor 72 who controls and operates the terminal device 70 that has sent the patient data, and who will correct the patient's cornea using the orthokeratology lens.

Table 1 shows the types of output data from the lens movement data acquiring device 22, data that is outputted from the selecting device 20 and stored in the database server 30, and data that is outputted from the terminal device 70 and inputted to the lens designating server 50.

TABLE 1

| Data from lens movement data acquiring device | Movement speed data Movement direction data | |
|---|---|---|
| Registered lens data (database) | Registered lens correction D data Registered lens movement data Registration stage data | |
| | Registered patient data | Registered myopia or hyperopia data Registered cornea D data Registered corneal diameter data Registered pupil diameter data |
| Data from a terminal device | Patient data | Registered myopia or hyperopia data Registered cornea D data Registered corneal diameter data Registered pupil diameter data |
| | Patient stage data | |

A description will next be given of detailed individual devices in the designating and supplying system 10 sequentially.

As shown in FIG. 1, the selecting device 20 includes a patient data acquiring device 20B having a keratometer (not illustrated), the lens movement data acquiring device 22 having a lens imaging camera 24 and a lens movement data detecting device 26, and the assessing device 28. In FIG. 1, the reference numeral 20A indicates an IF means, the reference numeral 21A indicates a keyboard, the reference numeral 2-B indicates a display, and the reference numeral 21C indicates a printer.

The lens imaging camera 24 is configured to image an orthokeratology lens mounted on a cornea at a position centering on a pupil of a patient whose head is in an erect state, to continuously or intermittently acquire images of the orthokeratology lens that is moving on the cornea.

The lens movement data detecting device 26 is configured to detect lens movement data, which includes data about at least a movement speed and a movement direction of the orthokeratology lens, from the images of the orthokeratology lens moving on the cornea, acquired by the lens imaging camera 24.

The assessing device 28 determines whether or not the lens movement data acquired by the lens movement data acquiring device 22, including the lens movement data detecting device 26, is within a certain range. An orthokeratology lens the movement of which is within the certain range is assessed to be suited for use for the patient.

Figure 3:
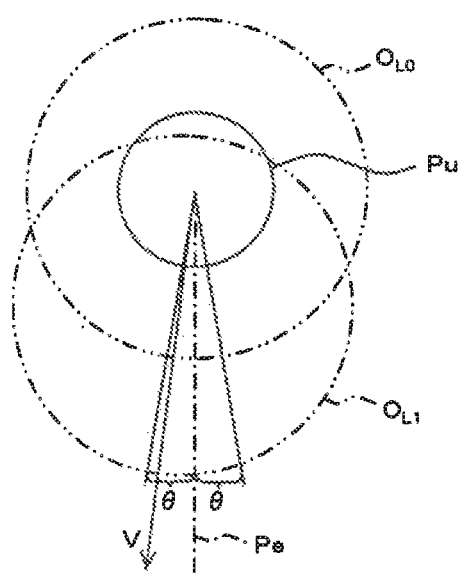
FIG. 3 is a plan view schematically illustrating a movement state of the orthokeratology lens mounted on a cornea of a patient.

In the certain range, for example, as illustrated in FIG. 3, conditions that a movement speed is more than 0 and 10 mm/sec or less, and a movement direction V is within an angle θ of 6 degrees or less rightward or leftward with respect to a normal Pe that extends perpendicularly downward from a pupil Pu, are satisfied. In FIG. 3, the reference numeral $O_{L0}$ represents the orthokeratology lens at the position of the pupil Pu, and the reference numeral $O_{L1}$ represents the orthokeratology lens that has moved from the position of the pupil Pu to the V direction.

An orthokeratology lens that has descended from the pupil position, while a patient is sleeping or waking, returns to the pupil position by blinking. However, when the above-described conditions are not satisfied, in other words, when the orthokeratology lens has descended too fast or too obliquely, the orthokeratology lens does not return to the pupil position by blinking. When the movement speed is 0, the orthokeratology lens that is in tight contact with a cornea causes a reduced oxygen supply to the cornea, and therefore the orthokeratology lens is not appropriate. The maximum movement speed of 10 mm/sec and the angle of 6 degrees are on the basis of treatment data of ten thousand or more patients given by the inventor.

To the assessing device 28, stage data that represents whether an orthokeratology lens to be used for a patient is a first lens, which is mounted on a cornea in a first stage of a plurality of correction stages, or a second or later lens, which is put in a second or later stage, is inputted from, for example, the keyboard 21A.

The selecting device 20 is configured to output, about an orthokeratology lens (registered lens) that is assessed to be suited for use for a patient, lens correction D data at a portion in contact with the patient's cornea, lens movement data, stage data, and patient data including myopia or hyperopia data that represents whether the orthokeratology lens is used for correction of myopia or hyperopia and presbyopia, cornea D data comprising cornea D data of the cornea to be corrected at the contact portion, corneal diameter data about a corneal diameter, and pupil diameter data about a pupil diameter to the database server 30.

The database server 30 is configured to accumulate the inputted data about the orthokeratology lens, more specifically, the registered lens movement data, the registered lens correction D data, the registration stage data, and the registered patient data including the registered lens movement data, the registered myopia or hyperopia data, the registered cornea D data, the registered corneal diameter data, and the registered pupil diameter data as shown in, for example, Table 2, to build the database 30B.

The database 30B is configured to include a registered lens correction D data memory means 31, a registered lens movement data memory means 32, a registration stage data memory means 33, a registered patient data memory means 34, and a registration cornea D and lens D difference data memory means 35.

In the present specification, for example, the registered lens correction D data accepting function 41 constitutes a registered lens correction D data accepting means together with the IF means 30A. In other words, each function constitutes a means together with the IF means.

TABLE 2

| | Registered patient data | | | | | |
|---|---|---|---|---|---|---|
| Lens No. | Registered myopia or hyperopia data | Registered patient cornea diopter ($D_r$) | Registered corneal diameter (mm) | Registered pupil diameter (mm) | Registered lens correction D data Diopter ($D_R$) | Registration stage data (Nth lens) |
| 10001 | CLOSE | 39.00 | 11.0 | 6.2 | 32.25 | 5 |
| 10002 | CLOSE | 39.30 | 10.8 | 6.4 | 34.10 | 2 |
| 10003 | CLOSE | 39.50 | 10.8 | 6.4 | 35.00 | 2 |
| 10004 | CLOSE | 40.05 | 10.8 | 6.4 | 33.75 | 4 |
| 10005 | CLOSE | 40.25 | 11.0 | 6.2 | 31.30 | 5 |
| 10006 | CLOSE | 40.40 | 10.8 | 6.4 | 32.90 | 4 |
| 10007 | CLOSE | 40.50 | 11.2 | 6.2 | 32.20 | 4 |
| 10008 | CLOSE | 40.50 | 11.2 | 6.6 | 32.25 | 3 |
| 10009 | CLOSE | 40.60 | 11.0 | 6.4 | 33.10 | 3 |
| 10010 | CLOSE | 41.10 | 11.2 | 6.2 | 33.80 | 4 |
| 10011 | CLOSE | 41.00 | 11.2 | 6.6 | 34.00 | 3 |
| 10012 | CLOSE | 41.00 | 11.0 | 6.4 | 34.70 | 3 |
| 10013 | CLOSE | 41.15 | 11.0 | 6.4 | 35.50 | 2 |
| 10014 | CLOSE | 41.20 | 10.8 | 6.2 | 36.00 | 2 |
| 10015 | CLOSE | 41.25 | 11.0 | 6.6 | 34.45 | 2 |
| 10016 | CLOSE | 41.30 | 10.8 | 6.0 | 35.70 | 2 |
| 10017 | CLOSE | 41.50 | 10.8 | 6.6 | 38.75 | 1 |
| 10018 | CLOSE | 41.75 | 10.8 | 6.6 | 39.50 | 1 |
| 10019 | CLOSE | 42.25 | 10.8 | 6.6 | 39.25 | 1 |
| 10020 | CLOSE | 42.50 | 10.8 | 6.4 | 39.25 | 1 |
| 13001 | DISTANT | 43.25 | 10.8 | 6.4 | 45.80 | 1 |
| 13002 | DISTANT | 43.50 | 10.8 | 6.4 | 47.50 | 1 |
| 13003 | DISTANT | 44.30 | 10.6 | 6.4 | 48.30 | 1 |
| 13004 | DISTANT | 45.00 | 10.6 | 6.4 | 48.60 | 1 |
| 13005 | DISTANT | 45.75 | 10.8 | 6.4 | 49.75 | 2 |
| 13006 | DISTANT | 45.80 | 10.6 | 6.4 | 49.00 | 1 |
| 13007 | DISTANT | 46.00 | 10.8 | 6.4 | 49.40 | 2 |
| 13008 | DISTANT | 46.25 | 10.6 | 6.4 | 49.25 | 1 |
| 13009 | DISTANT | 46.30 | 10.8 | 6.4 | 49.70 | 2 |
| 13010 | DISTANT | 46.45 | 10.8 | 6.4 | 49.60 | 2 |

Figure 4A:
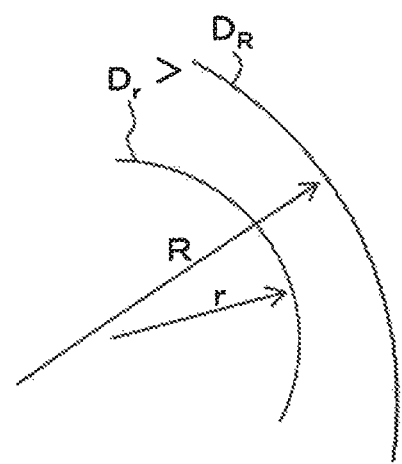
FIG. 4A is an enlarged cross-sectional view schematically illustrating the relationship between patient cornea D based on patient data and lens correction D of the orthokeratology lens in the case of correcting myopia.
Figure 4B:
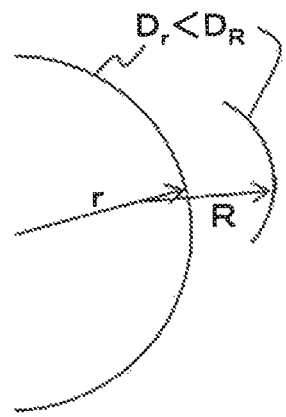
FIG. 4B is an enlarged cross-sectional view schematically illustrating the relationship between patient cornea D based on patient data and lens correction D of the orthokeratology lens in the case of correcting hyperopia or presbyopia.

Since the radius R of curvature of a lens and the radius r of curvature of a cornea increase with a decrease in diopter (D), in the case of correcting myopia, as shown in FIG. 4A, the relationship of lens diopter $D_R$ relative to corneal diopter $D_r$ is $D_r > D_R$ i.e. $r < R$ holds true. In the case of correcting hyperopia or presbyopia, as shown in FIG. 4B, $D_r < D_R$ i.e. $r > R$ holds true. The difference between $D_r$ and $D_R$, i.e. $D_r - D_R$ or $D_R - D_r$, differs depending on which stage of the plurality of correction stages the lens is used in, and the difference is the largest in the first stage.

Figure 2:
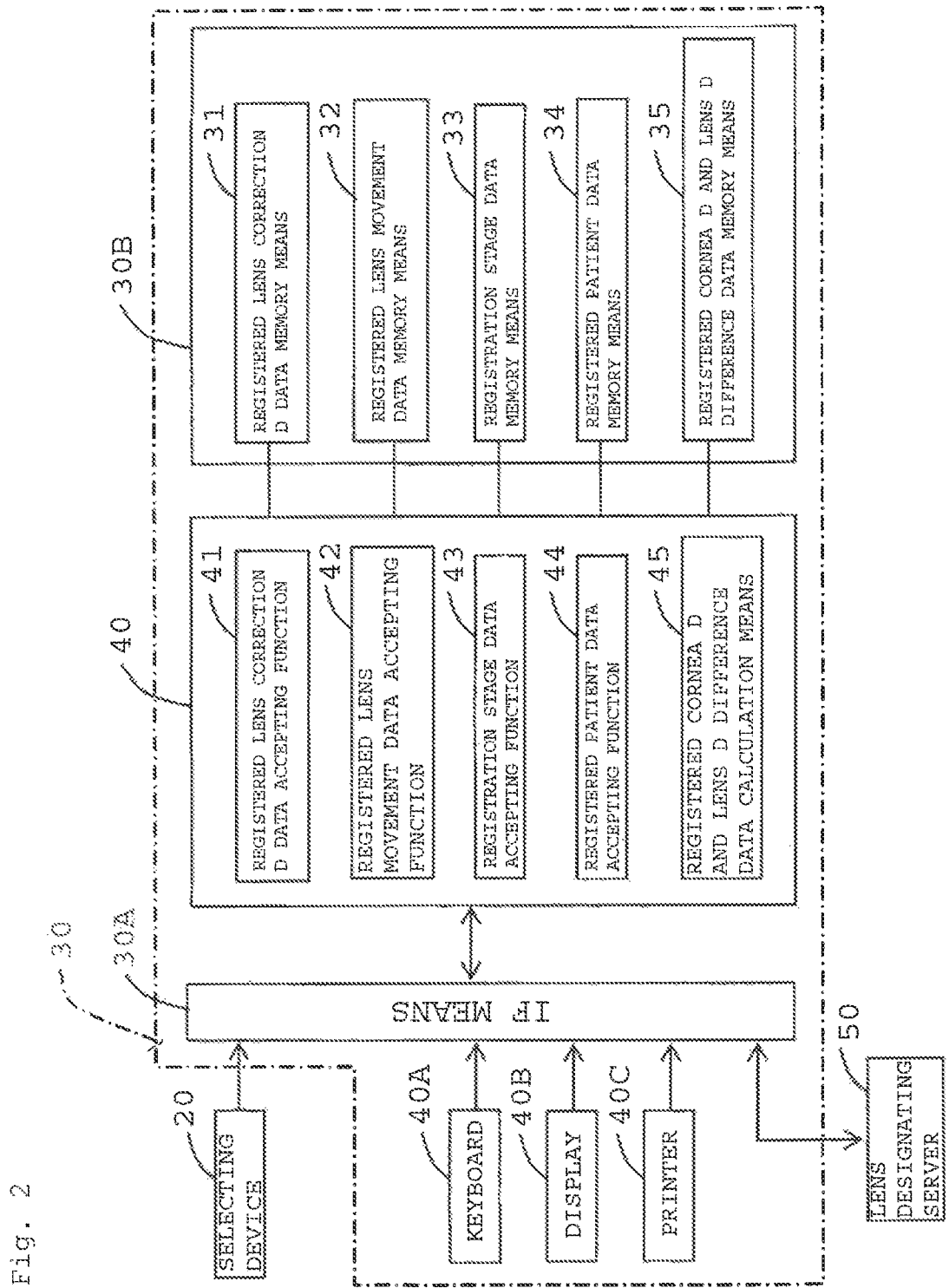
FIG. 2 is a block diagram showing a configuration of a database server according to the embodiment.

More specifically, as shown in FIG. 2, the database server 30 is configured to include an IF means 30A, a control means 40, and the database 30B. In FIG. 2, the reference numeral 40A indicates a keyboard, the reference numeral 40B indicates a display, and the reference numeral 40C indicates a printer.

The control means 40 is configured to include a registered lens correction D data accepting function 41, a registered lens movement data accepting function 42, a registration stage data accepting function 43, a registered patient data accepting function 44, and a registered cornea D and lens D difference data calculation means 45.

The registered lens correction D data accepting function 41 of the database server 30 is configured to accept registered lens correction D data transmitted from the selecting device 20 through the IF means 30A. The accepted registered lens correction D data is stored in the registered lens correction D data memory means 31 of the database 30B.

In the same manner, registered lens movement data transmitted from the selecting device 20 is accepted by the registered lens movement data accepting function 42, and stored in the registered lens movement data memory means 32. Registration stage data transmitted from the selecting device 20 is accepted by the registration stage data accepting function 43, and stored in the registration stage data memory means 33. Registered patient data is accepted by the registered patient data accepting function 44, and stored in the registered patient data memory means 34. The registration cornea D and lens D difference data calculation means 45 is configured to calculate the difference between registered cornea D data and registered lens correction D data of the registered patient data. A calculated result value is stored in the registration cornea D and lens D difference data memory means 35 as cornea D and lens D difference data.

Figure 5:
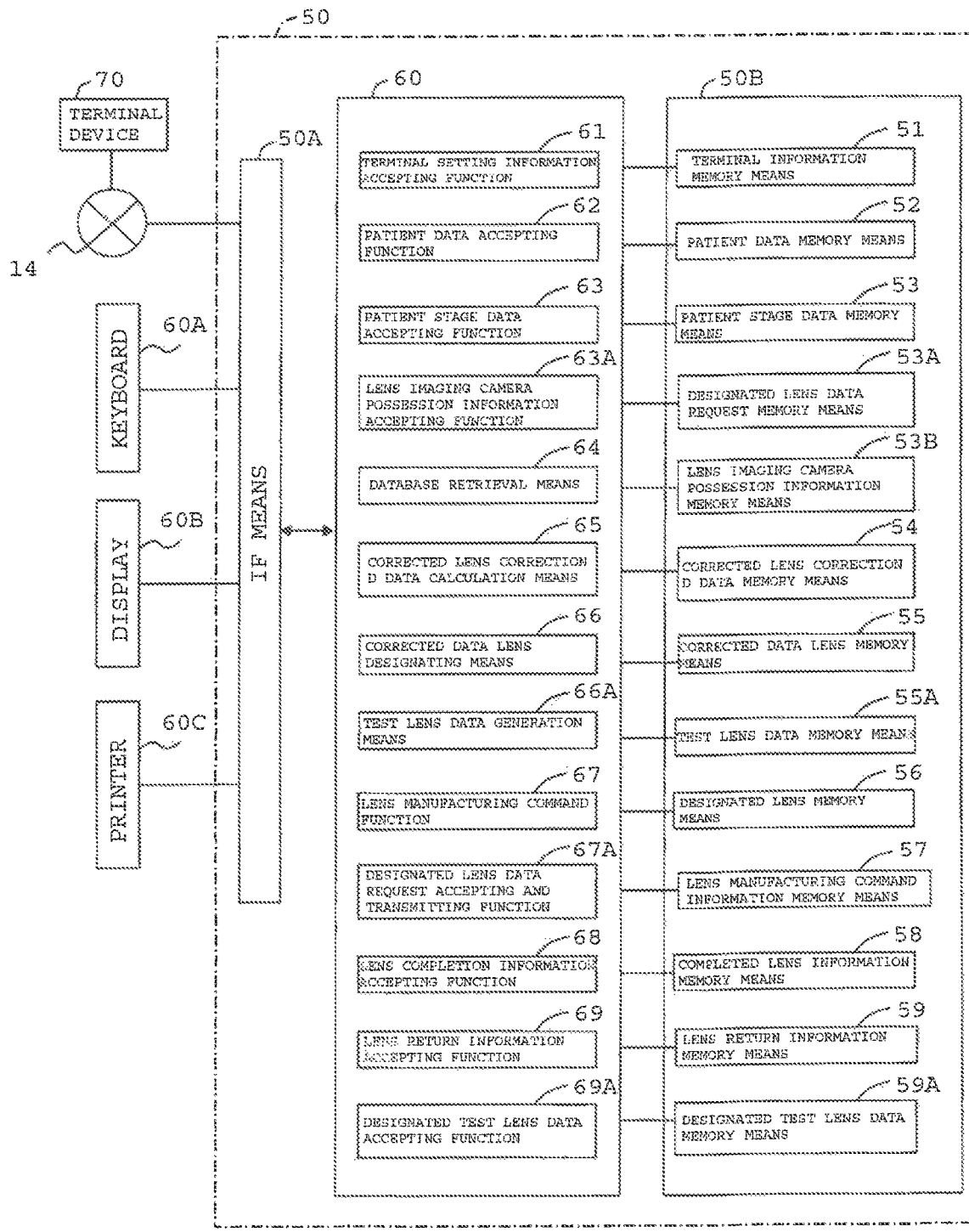
FIG. 5 is a block diagram illustrating a configuration of a lens designating server according to the embodiment.

A description will next be given of the lens designating server 50 shown in FIG. 5 in detail.

The lens designating server 50 is configured to include an IF means 50A, a control means 60, and a memory device 50B. In FIG. 5, the reference numeral 60A indicates a keyboard, the reference numeral 60B indicates a display, and the reference numeral 60C indicates a printer.

The control means 60 is configured to be capable of accepting a signal from the terminal device 70 through the Internet 14 and the IF means 50A as a response function of the control means 60.

From the keyboard 60A, a signal is manually inputted to the control means 60 through the IF means 50A.

The control means 60 is configured to include a terminal setting information accepting function 61, a patient data accepting function 62, a patient stage data accepting function 63, a lens imaging camera possession information accepting function 63A, a database retrieval means 64, a corrected lens correction D data calculation means 65, a corrected data lens designating means 66, a test lens data generation means 66A, a lens manufacturing command function 67, a designated lens data request accepting and transmitting function 67A, a lens completion information accepting function 68, a lens return information accepting function 69, and a designated test lens data accepting function 69A.

The memory device 50B is configured to include a terminal information memory means 51, a patient data memory means 52, a patient stage data memory means 53, a designated lens data request memory means 53A, a lens imaging camera possession information memory means 53B, a corrected lens correction D data memory means 54, a corrected data lens memory means 55, a test lens data memory means 55A, a designated lens memory means 56, a lens manufacturing command information memory means 57, a completed lens information memory means 58, a lens return information memory means 59, and a designated test lens data memory means 59A.

Figure 6:
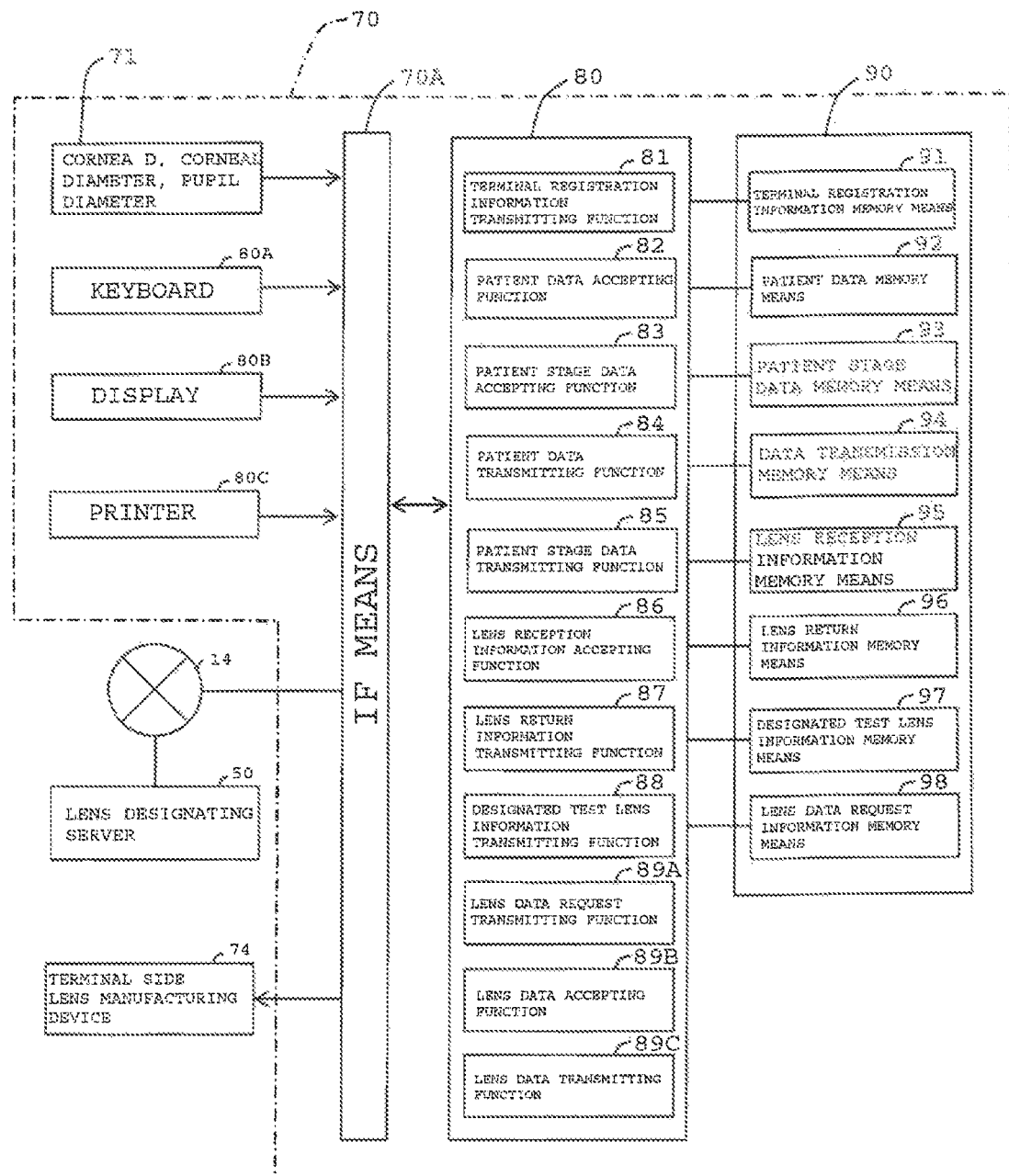
FIG. 6 is a block diagram illustrating a configuration of a terminal device according to the embodiment.

As shown in FIG. 6, the terminal device 70 includes a patient data acquiring device 71, a control device 80 having a patient data transmitting function 84, and a memory device 90. In FIG. 6, the reference numeral 70A indicates an IF means, the reference numeral 80A indicates a keyboard, the reference numeral 80B indicates a display, and the reference numeral 80C indicates a printer.

The control device 80 is configured to include a terminal registration information transmitting-function 81, a patient data accepting function 82, a patient stage data accepting function 83, the above-described patient data transmitting function 84, a patient stage data transmitting function 85, a lens reception information accepting function 86, a lens return information transmitting function 87, a designated test lens information transmitting function 88, and a lens data request transmitting function 89A, a lens data accepting function 89B, and a lens data transmitting function 89C that constitute the lens data accepting and transmitting device 73 together with an IF means 70A.

The memory device 90 is configured to include a terminal registration information memory means 91, a patient data memory means 92, a patient stage data memory means 93, a data transmission memory means 94, a lens reception information memory means 95, a lens return information memory means 96, a designated test lens information memory means 97, and a lens data request information memory means 98.

The terminal device 70 is configured to transmit information that the terminal device 70 is used by the contract doctor 72 and the terminal registration information transmitting function 81 is under the control of the doctor 72, to the lens designating server 50, which is a main server, together with a password and an ID. This terminal registration information is registered in the terminal registration information memory means 91 of the memory device 90. The terminal registration information includes information of whether or not the terminal device 70 includes a lens imaging camera that is similar to the lens imaging camera 24 of the selecting device 20.

The patient data accepting function 82 accepts patient data (patient data including patient cornea D data, corneal diameter, and pupil diameter) from the patient data acquiring device 71 through the IF means 70A. The accepted patient data is configured to be stored in the patient data memory means 92. Note that, out of the patient data, patient myopia or hyperopia data is inputted from the keyboard 80A.

Patient stage data is inputted from the keyboard 80A. The patient stage data is accepted by the patient stage data accepting function 83 through the IF means 70A, and stored in the patient stage data memory means 93.

The patient data transmitting function 84 is configured to transmit the patient data stored in the patient data memory means 92 to the lens designating server 50 through the IF means 70A and the Internet 14, and also the patient stage data transmitting function 85 is configured to transmit the patient stage data stored in the patient stage data memory means 93 to the lens designating server 50 through the IF means 70A and the Internet 14. The data transmission is stored in the data transmission memory means 94.

The lens reception information accepting function 86 accepts an input of information about a reception of an orthokeratology lens by the doctor 72, through the keyboard 80A and the IF means 70A, by an operation of the doctor 72. The lens reception information is stored in the lens reception information memory means 95 of the memory device 90.

The lens return information transmitting function 87 is configured to transmit information about a return of a lens, when the doctor 72 returns an orthokeratology lens that has been used for correcting a cornea in a completed correction stage to the lens dispatching agency 50D, on the basis of lens return information inputted from the keyboard 80A, to the lens designating server 50 through the IF means 70A and the Internet 14. The lens return information is stored in the lens return information memory means 96 of the memory device 90.

The designated test lens information transmitting function 88 is configured to transmit information about a test lens that is designated to be optimal for use in treatment, after a plurality of test lenses (described later) that have been sent are tried on a patient, to the lens designating server 50. This information is stored in the designated test lens information memory means 97.

The lens data request transmitting function 89A is configured to transmit a request signal to the lens designating server 50 when the doctor 72 requests lens data to manufacture an orthokeratology lens to be used for a patient. The lens data accepting function 89B is configured to transmit data of the designated orthokeratology lens, which is stored in the designated lens memory means 56, to the lens data accepting and transmitting device 73 through the IF means 50A.

The patient data acquiring device 71 is configured to acquire patient data which includes patient cornea D data of a patient's cornea to be corrected, corneal diameter data, and pupil diameter data. The patient data transmitting function 84 is configured to be capable of transmitting the patient data to the lens designating server 50 through the Internet 14.

More specifically, as the patient data acquiring device 71, Auto Kerato-Refractometer (KP-8100PA) manufactured by Topcon Corporation, Shin-Nippon (CT-1000) Corneal Topographer manufactured by, currently, Ajinomoto Trading, Inc., Pentacam Corneal Topographer manufactured by Oculuse, or the like is used.

The lens designating server 50 is configured to retrieve a registered lens used for a cornea that has the same patient cornea D data as or the closest patient cornea D data to the cornea in the database 30B, and designate the registered lens as an orthokeratology lens having a curvature suited for use for the patient.

Next, a database building process and an orthokeratology lens designating process will be described with reference to FIGS. 7 and 8.

Figure 7:
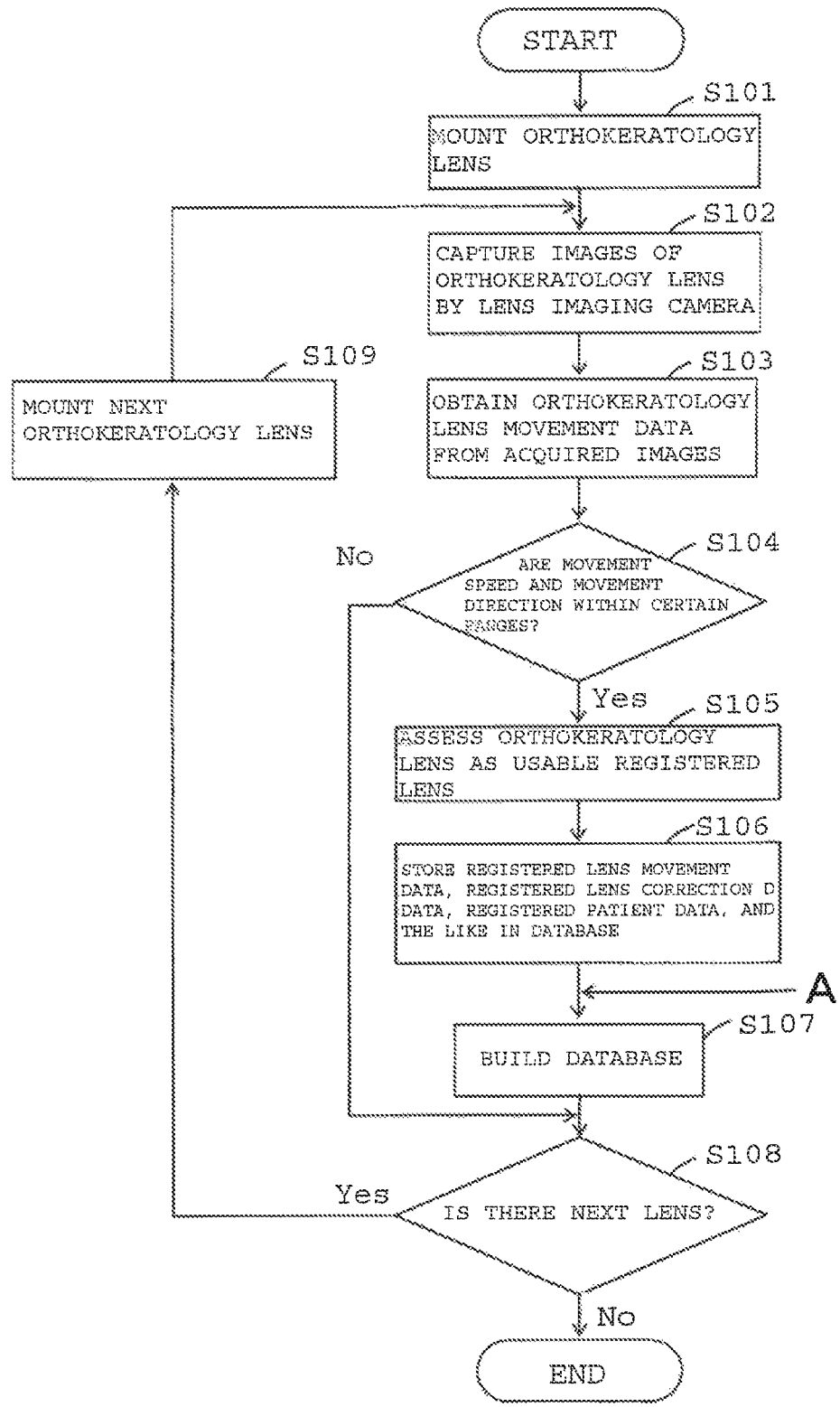
FIG. 7 is a flowchart of a database building process using data acquired by a selecting device according to the embodiment.

In the database building process, as shown in step S101 of FIG. 7, an orthokeratology lens is mounted on a patient's cornea to be corrected. At this time, the orthokeratology lens is mounted at a position centering on a pupil of the patient whose head is in an erect state. Then, the orthokeratology lens descends by gravity along a surface of the cornea. However, due to the relationship between a lens curvature of the orthokeratology lens and a corneal curvature of the cornea at a contact surface, the orthokeratology lens does not necessarily perpendicularly move downward, and its speed is not necessarily constant.

The present inventor has found out that, when conditions that a movement speed is more than 0 and 10 mm/sec or less, and a movement direction is within an angle of 6 degrees rightward or leftward with respect to a downward perpendicular normal of the pupil are satisfied as described above, the orthokeratology lens can be used for correction of the cornea.

Next, the process proceeds to step S102, and the lens imaging camera 24 images the orthokeratology lens mounted on the patient's cornea, to continuously or intermittently acquire images of the orthokeratology lens moving on the cornea. The process proceeds to step S103, and the lens movement data detecting device 26 acquires movement data, which includes a movement speed and a movement direction of the orthokeratology lens, from the image information acquired by the lens imaging camera 24.

Next, in step S104, the assessing device 28 determines whether or not the acquired movement data is within a certain range. To be more specific, it is determined whether or not the movement speed is more than 0 and 10 mm/sec or less, and the movement direction has an angle of 6 degree or less with respect to a normal passing through the center of the patient's pupil.

If a determination result is Yes, the process proceeds to the next step S105, and the orthokeratology lens is assessed to be a registered lens that can be used for correction of the cornea. If the determination result is No, the process proceeds to step S108.

When the orthokeratology lens is assessed to be usable for treatment in step S105, in the next step S106, the orthokeratology lens is assigned as a registered lens, and the assessing device 28 transmits registered lens correction D data, registered lens movement data, registration stage data, and registered patient data on the registered lens to the database server 30.

In the database server 30, the registered lens correction D data accepting function 41, the registered lens movement data accepting function 42, the registration stage data accepting function 43, and the registered patient data accepting function 44 accept the transmitted data, and store the data in the registered lens correction D data memory means 31, the registered lens movement data memory means 32, the registration stage data memory means 33, and the registered patient data memory means 34, respectively. By repetitions of the above processes, the database 30B is built.

Note that, in the control means 40 of the database server 30, the registration cornea D and lens D difference data calculation means 45 can calculate the difference between the patient cornea D data from the registered patient data and the lens correction D data of the orthokeratology lens to correct the patient's cornea, and a calculation result is stored in the registration cornea D and lens D difference data memory means 35 (refer to step S107).

As described above, the process of mounting the orthokeratology lens on the patient's cornea, the process of assessing whether or not the lens can be used, and the process of storing the assessed result in the database are repeated. If the next lens is absent in step S108, the database building process is completed. If the next lens is present, the process proceeds to step S109. The next orthokeratology lens is mounted, and the next steps S102 to S108 are repeated again.

Next, a process of designating an orthokeratology lens that is optimal for correction for a patient by the lens designating server 50, using data stored in the database 30B of the database server 30, on the basis of data transmitted from the terminal device 70 will be described.

Figure 8:
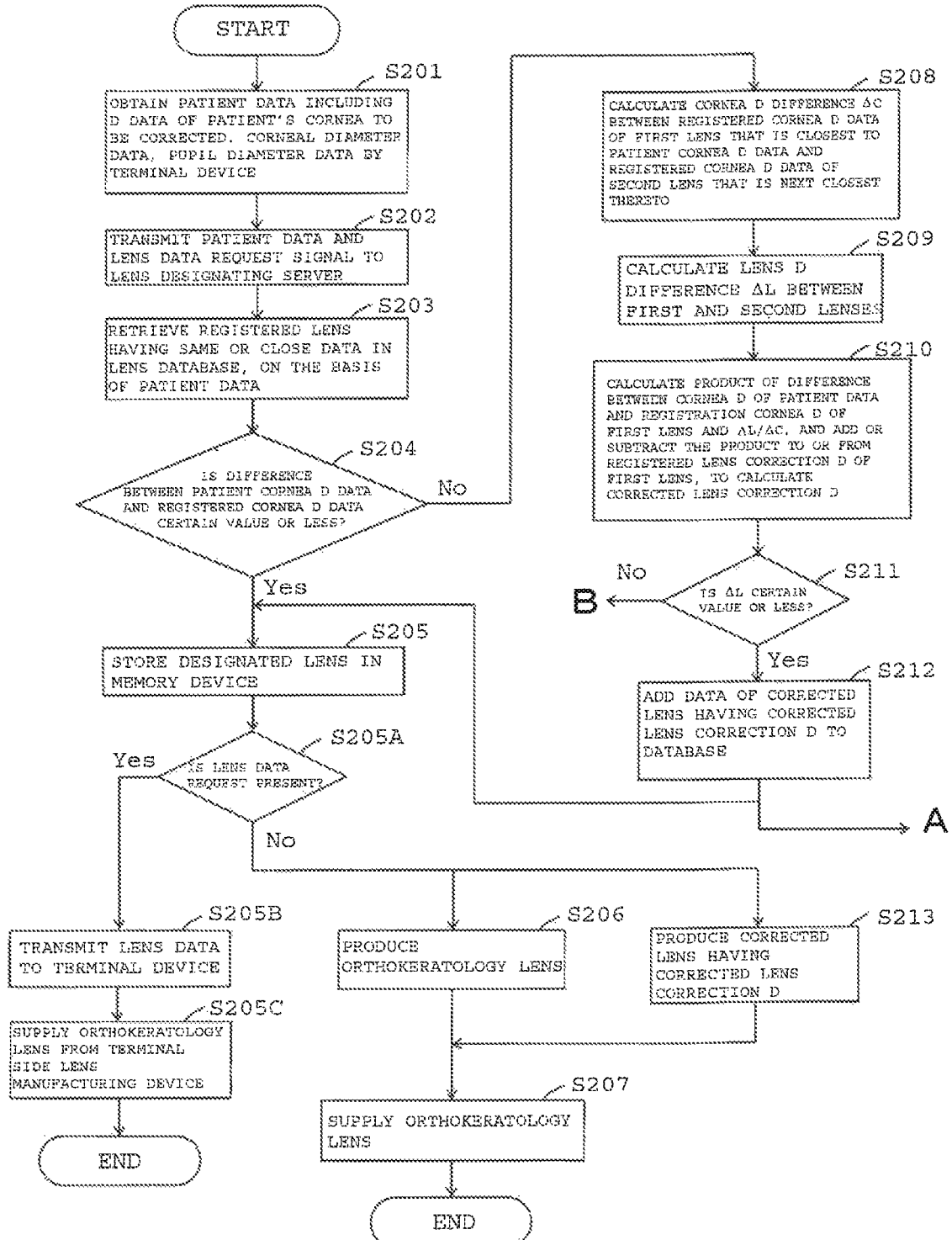
FIG. 8 is a flowchart of an optimal orthokeratology lens designating and supplying process, on the basis of data from a database and data from the terminal device, in the orthokeratology lens designating server according to the present embodiment.

As shown in FIG. 8, in step S201, in the terminal device 70, the patient data acquiring device 71 acquires patient data which includes patient cornea D data, a corneal diameter, and a pupil diameter of a patient who desires to correct his or her cornea. The patient data is transmitted to the lens designating server 50 through the Internet 14 (refer to step S202).

At this time, a doctor 72 inputs from the keyboard 80A data that indicates which stage of a plurality of correction stages the present cornea correction is in, to the patient stage data accepting function 83 through the IF means 70A. When the doctor 72 requires lens data to manufacture an orthokeratology lens designated by the lens designating server 50, lens data request information is inputted to the lens data request transmitting function 89A.

Note that the patient data from the patient data acquiring device 71 is once accepted by the patient data accepting function 82 through the IF means 70A. The accepted patient data and patient stage data are stored in the patient data memory means 92 and the patient stage data memory means 93, respectively. The lens data request information is stored in the lens data request information memory means 98.

The stored patient data and patient stage data are transmitted by the patient data transmitting function 84 and the patient stage data transmitting function 85 of the control device 80 of the terminal device 70 to the lens designating server 50 through the IF means 70A and the Internet 14, and also the lens data request information is transmitted by the lens data request transmitting function 89A thereof to the lens designating server 50 through the IF means 70A and the Internet 14.

In the lens designating server 50, the patient data and the patient stage data are accepted by the patient data accepting function 62 and the patient stage data accepting function 63 of the control means 60 and stored in the patient data memory means 52 and the patient stage data memory means 53 of the memory device 50B, respectively. The lens data request information is accepted by the designated lens data request accepting and transmitting function 67A, and stored in the designated lens data request memory means 53A of the memory device 50B. Furthermore, at the time of contracting with the doctor 72, if the doctor 72 has a lens imaging camera that is similar to the lens imaging camera 24, the information is inputted from the lens imaging camera possession information accepting function 63A, and stored in the lens imaging camera possession information memory means 53B.

The process proceeds to step S203, the database retrieval means 64 of the lens designating server 50 retrieves a registered lens having data that is the same as or similar to the patient data and the patient stage data from the terminal device 70, in the database 30B of the database server 30, on the basis of the patient data, or both of the patient data and the patient stage data transmitted from the terminal device 70.

The process proceeds to step S204, and it is determined that the difference between registered cornea D data of the retrieved registered lens and patient cornea D data of the patient data from the terminal device 70 is a certain value (for example, 0.03 D) or less.

If a determination result is Yes, the process proceeds to step S205. The registered lens is stored in the designated lens memory means 56 as a designated lens.

The above-described "difference" is 0.01 mm, i.e., a radius of curvature of the cornea. This is because it is considered that the detection accuracy limitation of a measurement device is 0.01 mm. Converting the radius of curvature into a diopter (D) in Table 3, 0.03 D is acquired.

TABLE 3

| Diopter (D) | mm |
|---|---|
| 36.00 | 9.38 |
| 36.12 | 9.34 |
| 36.25 | 9.31 |
| 36.37 | 9.28 |
| 36.50 | 9.25 |
| 36.62 | 9.22 |
| 36.75 | 9.18 |
| 37.00 | 9.12 |
| 37.12 | 9.09 |
| 37.25 | 9.06 |
| 37.37 | 9.03 |
| 37.50 | 9.00 |
| 37.62 | 8.97 |
| 37.75 | 8.94 |
| 37.87 | 8.91 |
| 38.00 | 8.88 |
| 38.12 | 8.85 |
| 38.25 | 8.82 |
| 38.37 | 8.80 |
| 38.50 | 8.77 |
| 38.62 | 8.74 |
| 38.75 | 8.71 |
| 38.87 | 8.68 |
| 39.00 | 8.65 |
| 39.12 | 8.63 |
| 39.25 | 8.60 |
| 39.37 | 8.57 |
| 39.50 | 8.55 |
| 39.62 | 8.52 |
| 39.75 | 8.49 |
| 39.87 | 8.47 |
| 40.00 | 8.44 |
| 40.12 | 8.41 |
| 40.25 | 8.39 |
| 40.37 | 8.36 |
| 40.50 | 8.33 |
| 40.62 | 8.31 |
| 40.75 | 8.28 |
| 40.87 | 8.26 |
| 41.00 | 8.23 |
| 41.13 | 8.21 |
| 41.25 | 8.18 |
| 41.38 | 8.16 |
| 41.50 | 8.13 |
| 41.63 | 8.11 |
| 41.75 | 8.08 |
| 41.88 | 8.06 |
| 42.00 | 8.04 |
| 42.13 | 8.01 |
| 42.25 | 7.99 |
| 42.38 | 7.96 |
| 42.50 | 7.94 |
| 42.63 | 7.92 |
| 42.75 | 7.89 |
| 42.88 | 7.87 |
| 43.00 | 7.85 |
| 43.13 | 7.83 |
| 43.25 | 7.80 |
| 43.38 | 7.78 |
| 43.50 | 7.76 |
| 43.63 | 7.74 |
| 43.75 | 7.71 |
| 43.88 | 7.69 |
| 44.00 | 7.67 |
| 44.13 | 7.65 |
| 44.25 | 7.63 |
| 44.38 | 7.61 |
| 44.50 | 7.58 |
| 44.63 | 7.56 |
| 44.75 | 7.54 |
| 44.88 | 7.52 |
| 45.00 | 7.50 |
| 45.13 | 7.48 |
| 45.25 | 7.46 |
| 45.38 | 7.44 |
| 45.50 | 7.42 |
| 45.63 | 7.40 |
| 45.75 | 7.38 |
| 46.00 | 7.34 |
| 46.13 | 7.32 |
| 46.25 | 7.30 |
| 46.38 | 7.28 |
| 46.50 | 7.26 |
| 46.63 | 7.24 |
| 46.75 | 7.22 |
| 46.88 | 7.20 |
| 47.00 | 7.18 |
| 47.13 | 7.16 |
| 47.25 | 7.14 |
| 47.38 | 7.12 |
| 47.50 | 7.11 |
| 47.63 | 7.09 |
| 47.75 | 7.07 |
| 47.88 | 7.05 |
| 48.00 | 7.03 |
| 48.13 | 7.01 |
| 48.25 | 6.99 |
| 48.38 | 6.98 |
| 48.50 | 6.96 |
| 48.63 | 6.94 |
| 48.75 | 6.92 |
| 48.88 | 6.91 |
| 49.00 | 6.89 |
| 49.13 | 6.87 |
| 49.25 | 6.85 |
| 49.38 | 6.84 |
| 49.50 | 6.82 |
| 49.63 | 6.80 |
| 49.75 | 6.78 |
| 49.88 | 6.77 |
| 50.00 | 6.75 |
| 50.13 | 6.73 |
| 50.25 | 6.72 |
| 50.38 | 6.70 |
| 50.50 | 6.68 |

TABLE 3-continued

| Diopter (D) | mm |
|---|---|
| 50.63 | 6.67 |
| 50.75 | 6.65 |

Note that, if there are a plurality of registered lenses, which is determined to be Yes, a registered lens having the closest registered corneal diameter data and registered pupil diameter data to the patient corneal diameter data and patient pupil diameter data, respectively, may be designated as a designated lens.

The process proceeds from step S205 to step S205A, and it is determined whether or not a lens data request from the doctor 72 is present. If No, the process proceeds to step S206.

In step S206, a command signal (lens data) to produce an orthokeratology lens having the same data as the stored designated lens is transmitted to the lens manufacturing device 50C, and therefore the orthokeratology lens is produced thereby.

If Yes in step S205A, in other words, if designated lens data request information is stored in the designated lens data request memory means 53A, the process proceeds to step S205B. A command signal is transmitted to the lens data accepting and transmitting device 73 of the terminal device 70 through the Internet 14. In step S205C, the command signal is transmitted from the lens data accepting and transmitting device 73 to the terminal side lens manufacturing device 74, and an orthokeratology lens is produced. In other words, the orthokeratology lens is produced in a distant location and used for treatment.

Note that, in the command signal, a diopter (D) of lens correction D data is converted into and outputted as a radius (mm) of curvature of a lens, with the use of a diopter-to-millimeter conversion table shown in Table 3.

The lens manufacturing device 50C and the terminal side lens manufacturing device 74 are devices that manufacture orthokeratology lenses on the basis of received data, and may be a normal cutting type contact lens manufacturing device or a 3D printer. The terminal side lens manufacturing device 74 is located by the doctor 72 or in a lens maker that has a cooperative relationship with the doctor 72, while the lens manufacturing device 50C is located in the vicinity of the lens designating server 50.

In step S207, the produced orthokeratology lens is directly provided to the doctor 72 or is supplied to the doctor 72 from the lens maker. Furthermore, when lens data is not requested, the orthokeratology lens is sent to the doctor 72 who manages the terminal device 70, through the lens dispatching agency 50D.

If the determination result is No in step S204, the process proceeds to step S208. Steps S208 to S210 are performed as follows by the corrected lens correction D data calculation means 65 of the control means 60 of the lens designating server 50.

Figure 9A:
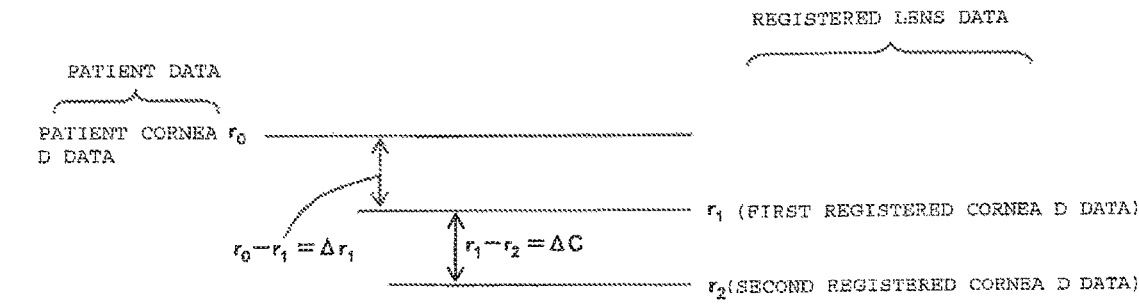
FIG. 9A is a graph showing a difference between cornea D data and lens correction D data, when calculating corrected lens correction D data.
Figure 9A:
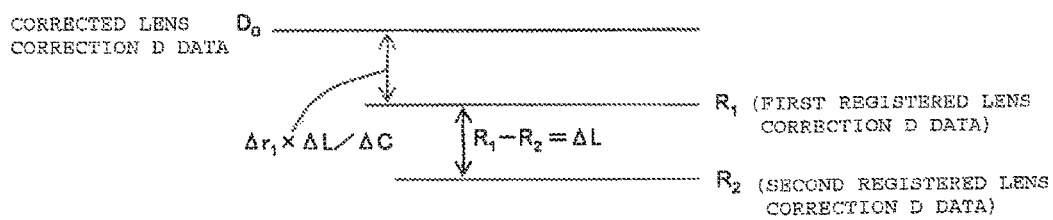
Figure 9B:
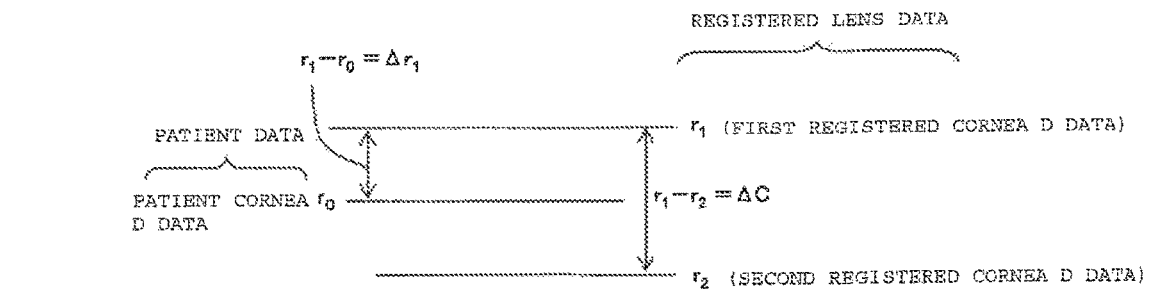
FIG. 9B is a graph similar to FIG. 9A, in different conditions.
Figure 9B:
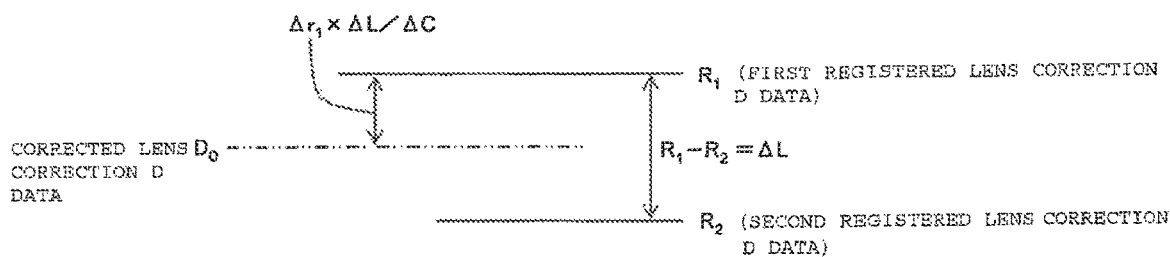

First, in step S208, as shown in FIGS. 9A and 9B, when the registered lens having data that is the closest to the cornea D data is assigned as a first lens, and the registered lens having data that is the second closest thereto is assigned as a second lens, the difference in cornea D data between first registered cornea D data $r_1$ of the first lens and second registered cornea D data $r_2$ of the second lens, i.e. $r_1-r_2=\Delta C$, is calculated. In the next step S209, when the registered lens correction D data of the first lens and the second lens is assigned as $R_1$ and $R_2$, respectively, the difference in registered lens correction D data, i.e., $R_1-R_2=\Delta L$, is calculated.

In step S210, the product of the difference $\Delta r_1$ between the patient cornea D data $r_0$ of the patient data and the registered cornea D data $r_1$ of the first lens and $\Delta L/\Delta C$ is obtained. The product is added to or subtracted from the registered lens correction D data $R_1$ of the first lens, to calculate corrected lens correction D data.

In other words, lens correction D per unit cornea D is calculated. Multiplying the lens correction D by $r_0-r_1=\Delta r_1$ results in a lens correction D value (difference) corresponding to the difference between $r_0$ and $r_1$, and $D_0$ is obtained by adding $R_1$ to this. For example, as shown in FIG. 9A, when $r_0>r_1>r_2$ and $R_1>R_2$, $D_0=(r_0-r_1=\Delta r_1)\times\Delta L/\Delta C+R_1$. When $r_1>r_0>r_2$ and $R_1>R_0>R_2$, as shown in FIG. 9B, $D_0=R_1-\Delta r_1\times\Delta L/\Delta C$.

Figure 10:
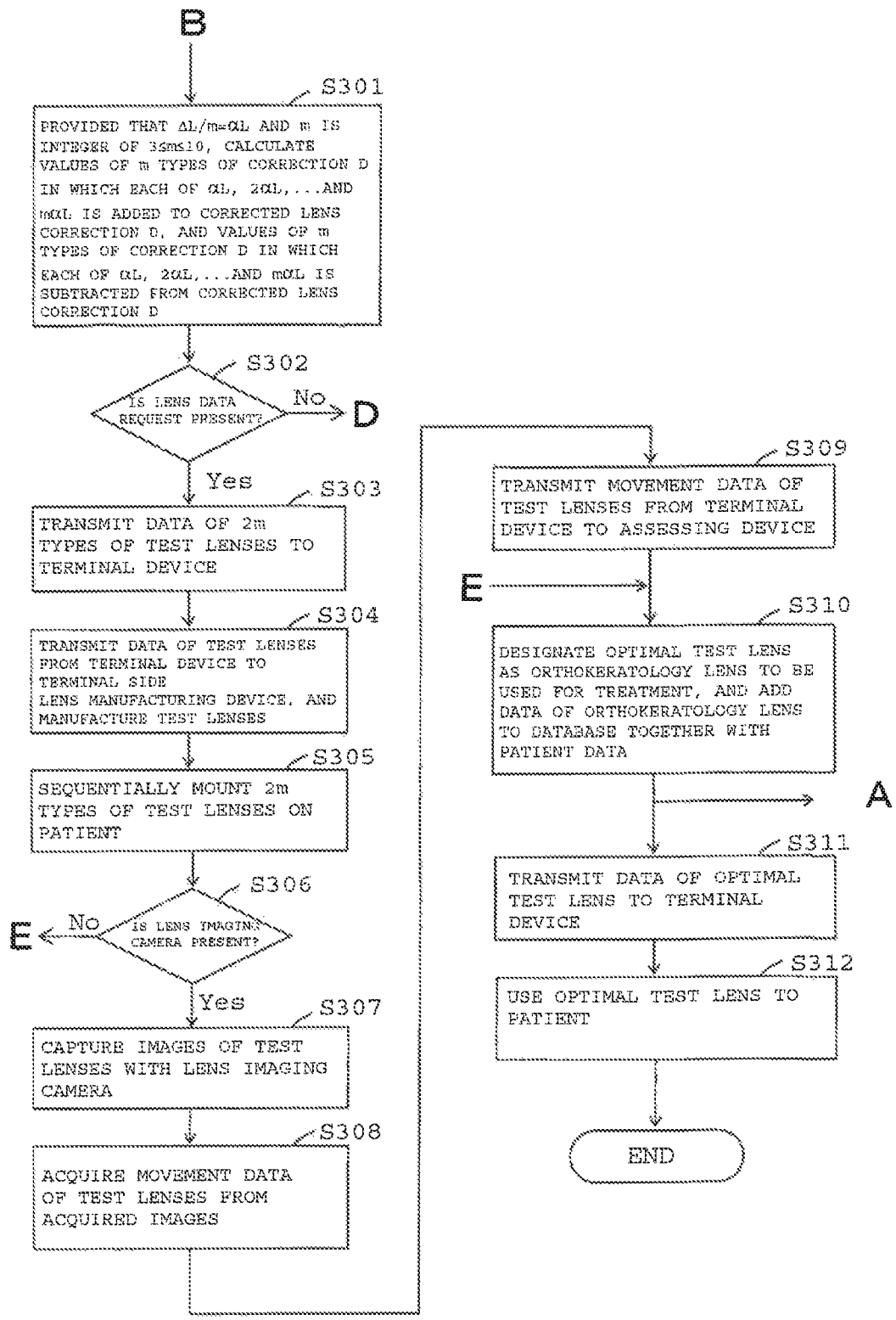
FIG. 10 is a flowchart of an orthokeratology lens designating process, when an estrangement between patient data and registered patient data is large.

In the next step S211, it is determined whether or not the above-described $\Delta L$ is a certain value or less, in other words, whether or not the difference between the registered lens correction D data of the first lens and that of the second lens is not too large. If the difference is too large, the corrected lens correction D data has low reliability. If the determination result is Yes, the process proceeds to step S212. If No, the process proceeds to a subroutine (B: FIG. 10).

In step S212, the corrected data lens designating means 66 designates a corrected orthokeratology lens having the corrected lens correction D data, which is calculated as described above, as a designated lens, and data of the designated lens is added to the database 30B, as indicated by symbol A in FIGS. 7 and 8. Next, the process returns to step S205, and the designated lens is stored in the memory device 50B. Next, in step S205A, the presence or absence of a lens data request is determined.

The corrected lens correction D data, the corrected data lens, and the designated lens may be stored in the corrected lens correction D data memory means 54, the corrected data lens memory means 55, and the designated lens memory means 56 of the memory device 50B, respectively, and may build a part of the database.

If the determination result is Yes in step S205A, an orthokeratology lens is supplied through the above-described steps S205B and S205C. If No, the process proceeds to step S213.

In step S213, the lens manufacturing command function 67 of the lens designating server 50 transmits a command signal to produce a corrected lens having the corrected lens correction D data, which is calculated as described above, to the lens manufacturing device 50C. The corrected lens is produced in step S213, and the process proceeds to step S207. In step S207, the corrected lens is sent from the lens dispatching agency 50D to the doctor 72.

Next, a case in which the determination result is No in step S211 will be described.

In this case, as indicated by symbol B, the process proceeds to step S301 shown in FIG. 10.

In step S301, the test lens data generation means 66A calculates production data for a plurality of test lenses.

Provided that $\Delta L/m=\alpha L$ and m is an integer of $3\leq m\leq 10$, m types of values, i.e., m types of correction D in which each of $\alpha L$, $2\alpha L$, ... and $m\alpha L$ is added to the corrected lens correction D (corrected lens correction D+$\alpha L$, corrected lens correction D+$2\alpha L$, ... corrected lens correction D+$m\alpha L$), and m types of values, i.e., m types of correction D in which each of $\alpha L$, $2\alpha L$, ... and $m\alpha L$ is subtracted from the corrected lens correction D (corrected lens correction D-$\alpha L$, corrected lens correction D-$2\alpha L$, ... corrected lens correction D-$m\alpha L$) are calculated.

Next, in step S302, the presence or absence of a lens data request is determined. If No, the process proceeds from symbol D to the subroutine of FIG. 11. If Yes, the process proceeds to step S303, and test lens data having the 2m types of correction D is transmitted to the terminal device 70.

In the next step S304, the test lens data is transmitted from the terminal device 70 to the terminal side lens manufacturing device 74, and test lenses are manufactured.

In step S305, the doctor 72 puts the test lens on a patient's eye.

In the next step S306, the doctor 72 determines whether or not the terminal device 70 has a lens imaging camera that is similar to the lens imaging camera 24 of FIG. 1. If Yes, the process proceeds to step S307, and the lens imaging camera captures an image of the test lens mounted on the patient.

The process proceeds to step S308, and movement data of the test lens is acquired from the image captured as described above. In the next step S309, the movement data is transmitted from the terminal device 70 to the assessing device 28 of the selecting device 20 through the Internet 14.

The process proceeds to step S310, data of an optimal test lens that is selected by the assessing device 28 is added to the database 30B, as an orthokeratology lens to be used for treatment, together with the patient data, by returning to the routine of FIG. 7 as indicated by symbol A.

To be more specific, the data of the selected orthokeratology lens to be used for treatment is transmitted from the terminal device 70 to the lens designating server 50. The data is accepted by the designated test lens data accepting function 69A of the lens designating server 50, and stored in the designated test lens data memory means 59A. The data of the orthokeratology lens to be used for treatment is transmitted from the lens designating server 50 to the control means 40 of the database server 30 (refer to FIG. 10 and symbol A of FIG. 7), together with the patient data, so that the data is added to the database 30B as registered lens data and registered patient data.

In step S311, the data of the optimal test lens is transmitted to the terminal device 70, and the doctor 72 uses a test lens having the transmitted data for the patient.

If No in step S306, as indicated by symbol E, the process proceeds to step S310. Data of an optimal test lens that is selected by decision of the doctor 72 as an orthokeratology lens to be used for treatment is added to the database 30B, together with the patient data, and the optimal test lens is used for the patient in step S312, through step S311.

Figure 11:
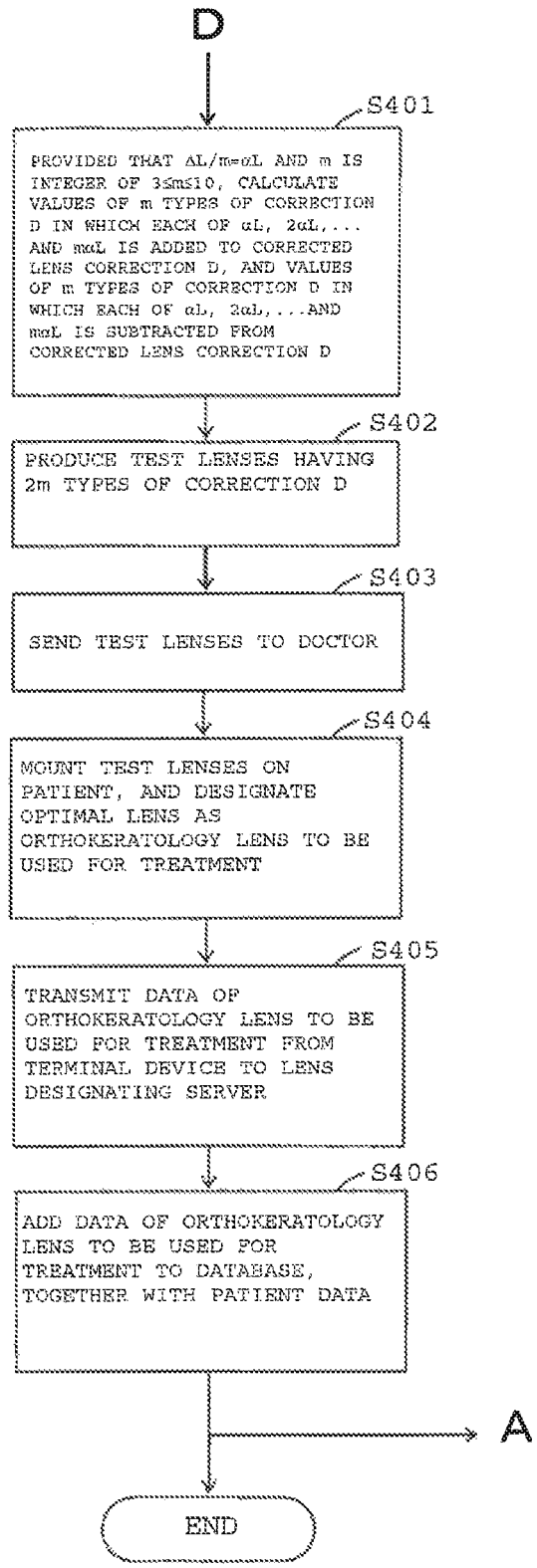
FIG. 11 is a flowchart of a subroutine of the process shown in FIG. 10.

Next, the determination result is No in step S302, as shown in symbol D, the process proceeds to step S401 in the subroutine of FIG. 11. Step S401 is the same as step S301 of FIG. 10.

In the next step S402, test lenses having the calculated 2m types of correction D are produced with the lens manufacturing device 50C.

The process proceeds to step S403, the manufactured test lenses are sent to the doctor 72. In step S404, the doctor 72 puts the test lenses on the patient, to designate an optimal test lens to be used for treatment.

In the next step S405, data of the orthokeratology lens to be used for treatment is transmitted from the terminal device 70 to the lens designating server 50.

The process proceeds to the next step S406, the data of the orthokeratology lens to be used for treatment is added to the database 30B, together with the patient data.

Note that, according to clinical trials of the present inventor, 6 to 10 types of test lenses are sufficient as test lenses having the 2m types of correction D.

The above-described designating and supplying system 10 includes the lens manufacturing device 50C and the terminal side lens manufacturing device 74, but the present invention is not limited thereto. The present invention may include a case in which the designating and supplying system 10 has only one of the lens manufacturing device 50C and the terminal side lens manufacturing device 74.

The present invention is applied to both of a case in which the lens imaging camera 24 is included as a part of the terminal device 70 and a case in which the lens imaging camera 24 is not included.

INDUSTRIAL APPLICABILITY

The present invention can be used for designating and manufacturing an orthokeratology lens for correcting a cornea, with a reduced patient's load.

REFERENCE SIGNS LIST

10 . . . orthokeratology lens designating and supplying system (designating and supplying system)
14 . . . the Internet
20 . . . selecting device
20A . . . IF means
20B . . . patient data acquiring device
21A, 40A, 60A, 80A . . . keyboard
21B, 40B, 60B, 80B . . . display
21C, 40C, 60C, 80C . . . printer
22 . . . lens movement data acquiring device
24 . . . lens imaging camera
26 . . . lens movement data detecting device
28 . . . assessing device
30 . . . database server
30A . . . IF means
30B . . . database
31 . . . registered lens correction D data memory means
32 . . . registered lens movement data memory means
33 . . . registration stage data memory means
34 . . . registered patient data memory means
35 . . . registration cornea D and lens D difference data memory means
40 . . . control means
41 . . . registered lens correction D data accepting function
42 . . . registered lens movement data accepting function
43 . . . registration stage data accepting function
44 . . . registered patient data accepting function
45 . . . registration cornea D and lens D difference data calculation means
50 . . . lens designating server
50A . . . IF means
50B, 90 . . . memory device
50C . . . lens manufacturing device
50D . . . lens dispatching agency
51 . . . terminal information memory means
52 . . . patient data memory means
53 . . . patient stage data memory means
53A . . . designated lens data request memory means
53B . . . lens imaging camera possession information memory means
54 . . . corrected lens correction D data memory means
55 . . . corrected data lens memory means
55A . . . test lens data memory means
56 . . . designated lens memory means
57 . . . lens manufacturing command information memory means
58 . . . completed lens information memory means 59 . . . lens return information memory means
59A . . . designated test lens data memory means
60 . . . control means
61 . . . terminal setting information accepting function
62 . . . patient data accepting function
63 . . . patient stage data accepting function
63A . . . lens imaging camera possession information accepting function
64 . . . database retrieval means
65 . . . corrected lens correction D data calculation means
66 . . . corrected data lens designating means
66A . . . test lens data generation means
67 . . . lens manufacturing command function
67A . . . designated lens data request accepting and transmitting function
68 . . . lens completion information accepting function
69 . . . lens return information accepting function
69A . . . designated test lens data accepting function
70 . . . terminal device
70A . . . IF means
71 . . . patient data acquiring device
72 . . . doctor
73 . . . lens data accepting and transmitting device
74 . . . terminal side lens manufacturing device
80 . . . control device
81 . . . terminal registration information transmitting function
82 . . . patient data accepting function
83 . . . patient stage data accepting function
84 . . . patient data transmitting function
85 . . . patient stage data transmitting function
86 . . . lens reception information accepting function
87 . . . lens return information transmitting function
88 . . . designated test lens information transmitting function
89A . . . lens data request transmitting function
89B . . . lens data accepting function
89C . . . lens data transmitting function
91 . . . terminal registration information memory means
92 . . . patient data memory means
93 . . . patient stage data memory means
94 . . . data transmission memory means
95 . . . lens reception information memory means
96 . . . lens return information memory means
97 . . . designated test lens information memory means
98 . . . lens data request information memory means

The invention claimed is:

1. An orthokeratology lens designating method comprising
a database building process of repeating a trial process in which a mounting process of mounting an orthokeratology lens on a cornea at a position centering on a pupil of a patient whose head is in an erect state, an image information acquiring process of continuously or intermittently acquiring images of the orthokeratology lens moving on the cornea, and a movement data detecting process of detecting a movement speed and a movement direction of the orthokeratology lens from the acquired image information are sequentially performed on a plurality of orthokeratology lenses, and a selection process of determining whether or not data of the acquired movement speed and movement direction is within a certain range, and when the data is within the certain range, selecting a lens as the orthokeratology lens to be used for the patient in order to build a lens database, provided that the selected orthokeratology lens is assigned as a registered lens, by storing registered patient data that includes at least registered cornea D data, out of registered lens correction D data having lens correction D data of the registered lens at a contact portion with the cornea, the registered cornea D data having D data of the cornea at the contact portion before mounting the registered lens, registered corneal diameter data having corneal diameter data of the patient, and registered pupil diameter data having pupil diameter data of the patient, and registration stage data having data that indicates in which stage of a plurality of correction stages, including first, second, and later stages, the registered lens is mounted on the cornea,
a patient data acquiring process of acquiring patient data including at least patient cornea D data, out of the patient cornea D data having D data of a patient's cornea to be corrected, patient corneal diameter data having data of a corneal diameter, and patient pupil diameter data having data of a pupil diameter,
a patient stage data acquiring process of acquiring patient stage data that indicates which stage of a plurality of correction stages the present mounting of an orthokeratology lens corresponds to, on the patient's cornea to be corrected, and
a lens designating process of retrieving the registered lens having the registered cornea D data that is the closest to the acquired patient cornea D data and the same registration stage data as the patient stage data in the lens database, and designating the retrieved registered lens as an orthokeratology lens to be used for the patient.

2. The orthokeratology lens designating method according to claim 1, wherein
the registered patient data in the database building process has registered myopia or hyperopia data that has data representing whether the registered lens is used for correction of myopia or hyperopia and presbyopia,
the patient data in the patient data acquiring process has patient myopia or hyperopia data that has data representing whether the lens is used for correction of myopia or hyperopia and presbyopia, and
the lens designating process retrieves the registered lens having the registered cornea D data that is the closest to the acquired patient cornea D data and the same registered myopia or hyperopia data and the same registration stage data as the registered myopia or hyperopia data and the patient stage data in the lens database, respectively and designates the retrieved registered lens as an orthokeratology lens to be used for the patient.

3. The orthokeratology lens designating method according to claim 1, wherein
in the selection process in the database building process, when conditions that the movement speed is more than 0 and 10 mm/sec or less, and the movement direction is within an angle of 6 degrees or less rightward or leftward with respect to a normal that extends perpendicularly downward from a pupil, are satisfied, the lens is selected as the orthokeratology lens to be used for the patient.

4. The orthokeratology lens designating method according to claim 1, wherein
in the database building process, the lens database is built by storing cornea D and lens D difference data that is a difference between patient cornea D data of the cornea before mounting the orthokeratology lens and the registered lens correction D data of the mounted orthokeratology lens.

5. The orthokeratology lens designating method according to claim 1, wherein
   in the lens designating process, when a difference between the acquired patient cornea D data and the closest registered cornea D data is a certain value or more,
   the retrieved registered lens is assigned as a first lens, and the registered lens having the registered cornea D data that is the second closest to the acquired patient cornea D data is assigned as a second lens, and the registered cornea D data and the registered lens correction D data are assigned as first cornea D data and first lens correction D data in the first lens, and are assigned as second cornea D data and second lens correction D data in the second lens, and
   a lens D difference per unit cornea D is calculated by a ratio between cornea D difference data between the first cornea D data and the second cornea D data and lens correction D difference data between the first lens correction D data and the second lens correction D data,
   corrected lens D data is calculated by adding or subtracting a product of the lens D difference and a difference between the patient cornea D data in the acquired patient data and the first cornea D data to or from the first lens correction D data, and
   the orthokeratology lens having this corrected lens D data is designated as the orthokeratology lens to be used for the patient.

6. The orthokeratology lens designating method according to claim 5, comprising:
   a process of calculating, when the lens D difference ΔL between the first lens correction D data and the second lens correction D data is a certain value or more, values of m types of correction D in which each of αL, 2αL, . . . and mαL is added to the corrected lens D data, and m types of correction D in which each of αL, 2αL, . . . and mαL is subtracted from the corrected lens D data provided that ΔL/m=αL and m is an integer of 3≤m≤10;
   a process of producing test lenses having the respective 2m types of correction D; and
   a process of trying the 2m types of test lenses on the patient to designate the optimal test lens as the orthokeratology lens for use in treatment.

7. The orthokeratology lens designating method according to claim 5, wherein
   in the database building process, the lens D data, the patient data, and the stage data about the orthokeratology lens designated on a basis of the lens D difference is stored to build the lens database.

8. The orthokeratology lens designating method according to claim 5, comprising:
   a lens manufacturing process of manufacturing a corrected orthokeratology lens on a basis of the corrected lens D data.

9. An orthokeratology lens designating and supplying method comprising,
   an orthokeratology lens designating method in claim 1,
      a registered lens correction D data transmitting process of transmitting the registered lens correction D data of the designated orthokeratology lens to a lens manufacturing device, and
      a lens manufacturing process of accepting the transmitted registered lens correction D data, and manufacturing the orthokeratology lens to be used for the patient on the basis of the registered lens correction D data.

10. The orthokeratology lens designating and supplying method according to claim 9, comprising
   a patient data transmitting process of transmitting the patient data and the patient stage data acquired in the patient data acquiring process and the patient stage data acquiring process, to a lens designating server that executes the lens designating process through the Internet.

11. The orthokeratology lens designating and supplying method according to claim 10, wherein
   in the registered lens correction D data transmitting process, the registered lens correction D data is transmitted to the lens manufacturing device directly or through the Internet from the lens designating server and the manufactured orthokeratology lens is sent for the patient.

12. The orthokeratology lens designating and supplying method according to claim 9, wherein
   the lens manufacturing process comprises:
   a process of receiving the registered lens correction D data transmitted in the registered lens correction D data transmitting process by a terminal device that executes the patient data acquiring process; and
   a registered lens correction D data transmitting process of transmitting the received registered lens correction D data to the lens manufacturing device.

13. The orthokeratology lens designating and supplying method according to claim 9, comprising
   a test lens data transmitting process of transmitting test lens data having the 2m types of correction D to the lens manufacturing device, and
   a test lens manufacturing process of manufacturing a test lens by the lens manufacturing device on a basis of the transmitted test lens data.

14. An orthokeratology lens designating system comprising a selecting device, a database server, a lens designating server connected to the database server, and a terminal device that can be connected to the lens designating server,
   the selecting device includes a lens movement data acquiring device that includes a lens imaging camera configured to image an orthokeratology lens mounted on a cornea at a position centering on a pupil of a patient whose head is in an erect state to continuously or intermittently acquire images of the orthokeratology lens moving on the cornea, and a lens movement data detecting device configured to detect lens movement data having data about at least a movement speed and a movement direction of the orthokeratology lens from image information of the orthokeratology lens moving on the cornea acquired by the lens imaging camera; and
   an assessing device configured to determine whether or not the acquired lens movement data is within a certain range, and assess the orthokeratology lens that is within the certain range as an orthokeratology lens suited for use for the patient,
   the selecting device is configured such that, provided that the orthokeratology lens that is suited for use for the patient is assigned as a registered lens, registered lens correction D data having data of lens correction D of the registered lens at a contact portion with the cornea of the patient, registered patient data including at least registered cornea D data, out of the registered cornea D data having D data of the cornea to be corrected at the contact portion, registered corneal diameter data having corneal diameter data of the patient, and registered pupil diameter data, and registration stage data having data that indicates in which stage of a plurality of correction stages, including first, second, and later stages, the registered lens is mounted on the cornea are outputted to the database server, the database server is configured to build a database by storing the registered patient data and the registration stage data on the registered lens, the terminal device includes a patient data acquiring device configured to acquire patient data including at least patient cornea D data, out of the patient cornea D data having D data of a patient's cornea to be corrected, patient corneal diameter data having data of a corneal diameter, and patient pupil diameter data having data of a pupil diameter, and a patient stage data acquiring device configured to acquire patient stage data that indicates in which stage of the plurality of correction stages, including the first, second, and later stages, the next orthokeratology lens is mounted on the patient's cornea to be corrected, and the terminal device is configured to be capable of transmitting the patient data and the patient stage data to the lens designating server, and the lens designating server is configured to retrieve the registered lens having the registered cornea D data that is the closest to the acquired patient cornea D data and the same registration stage data as the patient stage data in the database, and designate the retrieved registered lens as an orthokeratology lens to be used for the patient.

15. The orthokeratology lens designating system according to claim 14, wherein the selecting device is configured to output registered myopia or hyperopia data that has data representing whether the registered lens is used for correction of myopia or hyperopia and presbyopia, to the database server, the database server is configured to build a database by storing the registered myopia or hyperopia data, the terminal device is configured to be capable of transmitting patient myopia or hyperopia data that has data representing whether the lens is used for correction of myopia or hyperopia and presbyopia, to the lens designating server, and the lens designating server is configured to retrieve the registered lens having the registered cornea D data that is the closest to the acquired patient cornea D data, the same registered myopia or hyperopia data as the acquired patient myopia or hyperopia data, and the same registration stage data as the acquired patient stage data from the database, and designate the retrieved registered lens as an orthokeratology lens to be used for the patient.

16. The orthokeratology lens designating system according to claim 15, wherein when conditions that the movement speed is more than 0 and 10 mm/sec or less, and the movement direction is within an angle of 6 degrees or less rightward or leftward with respect to a normal that extends perpendicularly downward from a pupil, are satisfied, the assessing device is configured to select the lens as the orthokeratology lens to be used for the patient.

17. The orthokeratology lens designating system according to claim 15, wherein the database server is configured to build a lens database by storing cornea D and lens D difference data that is a difference between patient cornea D data of the cornea before mounting the orthokeratology lens and the registered lens correction D data of the mounted orthokeratology lens.

18. The orthokeratology lens designating system according to claim 15, wherein the lens designating server is configured, when a difference between the acquired patient cornea D data and the registered cornea D data closest thereto is a certain value or more, to assign the retrieved registered lens as a first lens, and the registered lens having the registered cornea D data that is the second closest to the patient cornea D data in the acquired patient data as a second lens, to assign the registered cornea D data and the registered lens correction D data as first cornea D data and first lens correction D data in the first lens, and as second cornea D data and second lens correction D data in the second lens, and to calculate a lens correction D difference per unit cornea correction D data difference by a ratio between cornea D difference data between the first cornea D data and the second cornea D data and lens correction D difference data between the first lens correction D data and the second lens correction D data, to calculate corrected lens correction D data by adding or subtracting a product of the lens correction D difference and a difference between the patient cornea D data in the acquired patient data and the first cornea D data to or from the first lens correction D data, and to designate the orthokeratology lens having this corrected lens correction D data as the orthokeratology lens to be used for the patient.

19. The orthokeratology lens designating system according to claim 18, wherein the lens designating server is configured to calculate, when the lens D difference $\Delta L$ between the first lens correction D data and the second lens correction D data is a certain value or more, values of m types of correction D in which each of $\alpha L, 2\alpha L, \ldots$ and $m\alpha L$ is added to the corrected lens correction D, and m types of correction D in which each of $\alpha L, 2\alpha L, \ldots$ and $m\alpha L$ is subtracted from the corrected lens correction D provided that $\Delta L/m=\alpha L$ and m is an integer of $3 \le m \le 10$, and to output data for manufacturing test lenses having the respective 2m types of correction D.

20. The orthokeratology lens designating system according to claim 19, wherein the lens designating server is configured to send the data for manufacturing test lenses having the respectively 2m types of correction D to the lens manufacturing device.

21. The orthokeratology lens designating system according to claim 18, wherein the database server is configured to build the lens database by storing the corrected lens correction D data, the patient data, and the patient stage data about the orthokeratology lens designated on a basis of the lens correction D difference data as the registered lens correction D data, registered patient data, and registered stage data, respectively.

22. The orthokeratology lens designating system according to claim 15, wherein the lens movement data detecting device is an image analysis device, and the selecting device is a central controlling device that stores data of allowable values for the movement speed and the movement direction in advance.

23. The orthokeratology lens designating system according to claim 14, further comprising:
a lens manufacturing device, wherein
the lens manufacturing device is configured to manufacture the same orthokeratology lens to be mounted on the patient as the registered lens, on a basis of the registered lens correction D data of the designated orthokeratology lens.

24. The orthokeratology lens designating system according to claim 23, wherein the terminal device includes a lens data accepting and transmitting device configured to accept the registered lens correction D data of the registered lens corresponding to the designated orthokeratology lens transmitted from the lens designating server, and to output the accepted registered lens correction D data to the lens manufacturing device.

25. The orthokeratology lens designating system according to claim 24, wherein the lens manufacturing device is annexed to the terminal device.

26. The orthokeratology lens designating system according to claim 25, wherein the terminal device includes a lens data request transmitting function that requests the lens designating server to send the lens data of the registered lens designated as the orthokeratology lens to the terminal device.

27. The orthokeratology lens designating system according to claim 23, wherein the lens manufacturing device is configured to accept directly or through the Internet the registered lens correction D data from the lens designating server.

* * * * *